United States Patent
Tan et al.

(10) Patent No.: US 9,861,980 B2
(45) Date of Patent: Jan. 9, 2018

(54) FLUID MIXING AND DELIVERY IN MICROFLUIDIC SYSTEMS

(71) Applicant: OPKO Diagnostics, LLC, Woburn, MA (US)

(72) Inventors: Enqing Tan, Lexington, MA (US); Vincent Linder, Tewksbury, MA (US); Jason Taylor, Windham, NH (US); David Steinmiller, Mountain View, CA (US)

(73) Assignee: OPKO Diagnostics, LLC, Woburn, MA (US)

( * ) Notice: Subject to any disclaimer, the term of this patent is extended or adjusted under 35 U.S.C. 154(b) by 0 days.

(21) Appl. No.: 15/385,117

(22) Filed: Dec. 20, 2016

(65) Prior Publication Data

US 2017/0165664 A1 Jun. 15, 2017

Related U.S. Application Data

(63) Continuation of application No. 14/521,959, filed on Oct. 23, 2014, now Pat. No. 9,555,408, which is a (Continued)

(51) Int. Cl.
*F16K 11/02* (2006.01)
*B01L 3/00* (2006.01)

(52) U.S. Cl.
CPC ..... *B01L 3/502723* (2013.01); *B01L 3/50273* (2013.01); *B01L 3/502738* (2013.01); (Continued)

(58) Field of Classification Search
CPC ............. B01L 3/5027; B01L 3/502738; B01L 2300/0867; B01L 2400/0487; B01L 3/502723; B01F 13/0059; F16K 99/0001
(Continued)

(56) References Cited

U.S. PATENT DOCUMENTS 3,735,640 A    5/1973  Chizhov et al.
4,318,994 A    3/1982  Meyer et al.
(Continued)

FOREIGN PATENT DOCUMENTS

EP    0 110 771 B1    3/1988
EP    0 643 307 A1    3/1995
(Continued)

OTHER PUBLICATIONS

International Search Report and Written Opinion for PCT/US2010/057969 dated Jan. 27, 2011.
(Continued)

*Primary Examiner* — Reinaldo Sanchez-Medina
(74) *Attorney, Agent, or Firm* — Wolf, Greenfield & Sacks, P.C.

(57) ABSTRACT

The specification generally discloses systems and methods for mixing and delivering fluids in microfluidic systems. The fluids can contain, in some embodiments reagents that can participate in one or more chemical or biological reactions. Some embodiments relate to systems and methods employing one or more vent valves to controllably flow and/or mix portions of fluid within the microfluidic system. Advantageously, fluid control such as a sequence of fluid flow and/or a change in flow rate, can be achieved by opening and closing one or more vent valves and by applying a single source of fluid flow (e.g., a vacuum) operated at a substantially constant pressure. This can simplify the operation and use of the device by an intended user.

20 Claims, 11 Drawing Sheets

Related U.S. Application Data continuation of application No. 14/039,786, filed on Sep. 27, 2013, now Pat. No. 8,915,259, which is a continuation of application No. 12/953,771, filed on Nov. 24, 2010, now Pat. No. 8,567,425.

(60) Provisional application No. 61/263,981, filed on Nov. 24, 2009.

(52) U.S. Cl.
CPC ............. *B01L 2200/0673* (2013.01); *B01L 2200/0684* (2013.01); *B01L 2300/0867* (2013.01); *B01L 2300/0877* (2013.01); *B01L 2400/0487* (2013.01); *B01L 2400/0694* (2013.01)

(58) Field of Classification Search
USPC ............... 137/3, 7, 597, 605, 806, 896, 897
See application file for complete search history.

(56) References Cited

U.S. PATENT DOCUMENTS

| | | |
|---|---|---|
| 4,517,302 A | 5/1985 | Saros |
| 4,963,498 A | 10/1990 | Hillman et al. |
| 5,051,237 A | 9/1991 | Grenner et al. |
| 5,205,322 A | 4/1993 | Merick et al. |
| 5,219,762 A | 6/1993 | Katamine et al. |
| 5,268,147 A | 12/1993 | Zabetakis et al. |
| 5,286,454 A | 2/1994 | Nilsson et al. |
| 5,376,252 A | 12/1994 | Ekström et al. |
| 5,478,751 A | 12/1995 | Oosta et al. |
| 5,486,335 A | 1/1996 | Wilding et al. |
| 5,571,410 A | 11/1996 | Swedberg et al. |
| 5,635,358 A | 6/1997 | Wilding et al. |
| 5,637,469 A | 6/1997 | Wilding et al. |
| 5,726,026 A | 3/1998 | Wilding et al. |
| 5,731,212 A | 3/1998 | Gavin et al. |
| 5,842,787 A | 12/1998 | Kopf-Sill et al. |
| 5,866,345 A | 2/1999 | Wilding et al. |
| 5,876,675 A | 3/1999 | Kennedy |
| 5,942,443 A | 8/1999 | Parce et al. |
| 5,955,028 A | 9/1999 | Chow |
| 5,957,579 A | 9/1999 | Kopf-Sill et al. |
| 6,019,944 A | 2/2000 | Buechler |
| 6,042,709 A | 3/2000 | Parce et al. |
| 6,046,056 A | 4/2000 | Parce et al. |
| 6,100,541 A | 8/2000 | Nagle et al. |
| 6,103,199 A | 8/2000 | Bjornson et al. |
| 6,136,272 A | 10/2000 | Weigl et al. |
| 6,146,489 A | 11/2000 | Wirth |
| 6,146,589 A | 11/2000 | Chandler |
| 6,168,948 B1 | 1/2001 | Anderson et al. |
| 6,176,962 B1 | 1/2001 | Soane et al. |
| 6,184,029 B1 | 2/2001 | Wilding et al. |
| 6,186,660 B1 | 2/2001 | Kopf-Sill et al. |
| 6,214,560 B1 | 4/2001 | Yguerabide et al. |
| 6,238,538 B1 | 5/2001 | Parce et al. |
| 6,241,560 B1 | 6/2001 | Furusawa et al. |
| 6,251,343 B1 | 6/2001 | Dubrow et al. |
| 6,274,337 B1 | 8/2001 | Parce et al. |
| 6,296,020 B1 | 10/2001 | McNeely et al. |
| 6,331,439 B1 | 12/2001 | Cherukuri et al. |
| 6,333,200 B1 | 12/2001 | Kaler et al. |
| 6,361,958 B1 | 3/2002 | Shieh et al. |
| 6,413,782 B1 | 7/2002 | Parce et al. |
| 6,416,642 B1 | 7/2002 | Alajoki et al. |
| 6,429,025 B1 | 8/2002 | Parce et al. |
| 6,432,720 B2 | 8/2002 | Chow |
| 6,479,299 B1 | 11/2002 | Parce et al. |
| 6,488,872 B1 | 12/2002 | Beebe et al. |
| 6,488,894 B1 | 12/2002 | Miethe et al. |
| 6,488,896 B2 | 12/2002 | Weigl et al. |
| 6,498,353 B2 | 12/2002 | Nagle et al. |
| 6,517,234 B1 | 2/2003 | Kopf-Sill et al. |
| 6,551,841 B1 | 4/2003 | Wilding et al. |
| 6,610,499 B1 | 8/2003 | Fulwyler et al. |
| 6,613,512 B1 | 9/2003 | Kopf-Sill et al. |
| 6,613,525 B2 | 9/2003 | Nelson et al. |
| 6,620,625 B2 | 9/2003 | Wolk et al. |
| 6,632,619 B1 | 10/2003 | Harrison et al. |
| 6,638,482 B1 | 10/2003 | Ackley et al. |
| 6,656,430 B2 | 12/2003 | Sheppard, Jr. et al. |
| 6,669,831 B2 | 12/2003 | Chow et al. |
| 6,705,357 B2 | 3/2004 | Jeon et al. |
| 6,709,869 B2 | 3/2004 | Mian et al. |
| 6,716,620 B2 | 4/2004 | Bashir et al. |
| 6,742,661 B1 | 6/2004 | Schulte et al. |
| 6,761,962 B2 | 7/2004 | Bentsen et al. |
| 6,780,584 B1 | 8/2004 | Edman et al. |
| 6,794,197 B1 | 9/2004 | Indermuhle et al. |
| 6,818,184 B2 | 11/2004 | Fulwyler et al. |
| 6,827,095 B2 | 12/2004 | O'Connor et al. |
| 6,828,143 B1 | 12/2004 | Bard |
| 6,830,936 B2 | 12/2004 | Anderson et al. |
| 6,858,185 B1 | 2/2005 | Kopf-Sill et al. |
| 6,878,271 B2 | 4/2005 | Gilbert et al. |
| 6,878,755 B2 | 4/2005 | Singh et al. |
| 6,911,183 B1 | 6/2005 | Handique et al. |
| 6,949,377 B2 | 9/2005 | Ho |
| 6,953,550 B2 | 10/2005 | Sheppard, Jr. et al. |
| 6,989,128 B2 | 1/2006 | Alajoki et al. |
| 7,005,292 B2 | 2/2006 | Wilding et al. |
| 7,015,046 B2 | 3/2006 | Wohlstadter et al. |
| 7,018,830 B2 | 3/2006 | Wilding et al. |
| 7,028,536 B2 | 4/2006 | Karp et al. |
| 7,067,263 B2 | 6/2006 | Parce et al. |
| 7,087,148 B1 | 8/2006 | Blackburn et al. |
| 7,091,048 B2 | 8/2006 | Parce et al. |
| 7,276,330 B2 | 10/2007 | Chow et al. |
| 8,030,057 B2 | 10/2011 | Linder et al. |
| 8,202,492 B2 | 6/2012 | Linder et al. |
| 8,389,272 B2 | 3/2013 | Linder et al. |
| 8,409,527 B2 | 4/2013 | Linder et al. |
| 8,567,425 B2 | 10/2013 | Tan et al. |
| 8,915,259 B2 | 12/2014 | Tan et al. |
| 9,075,051 B2 | 7/2015 | Tan et al. |
| 9,555,408 B2 | 1/2017 | Tan et al. |
| 2001/0036672 A1 | 11/2001 | Anderson et al. |
| 2002/0001818 A1 | 1/2002 | Brock |
| 2002/0019059 A1 | 2/2002 | Chow et al. |
| 2002/0031836 A1 | 3/2002 | Feldstein |
| 2002/0071788 A1 | 6/2002 | Fujii et al. |
| 2002/0092767 A1 | 7/2002 | Bjornson et al. |
| 2002/0142618 A1 | 10/2002 | Parce et al. |
| 2002/0199094 A1 | 12/2002 | Strand et al. |
| 2003/0005967 A1 | 1/2003 | Karp |
| 2003/0012697 A1 | 1/2003 | Hahn et al. |
| 2003/0082081 A1 | 5/2003 | Fouillet et al. |
| 2003/0118486 A1 | 6/2003 | Zhou et al. |
| 2003/0124623 A1 | 7/2003 | Yager et al. |
| 2003/0138969 A1 | 7/2003 | Jakobsen et al. |
| 2003/0207328 A1 | 11/2003 | Yguerabide et al. |
| 2004/0077074 A1 | 4/2004 | Ackley et al. |
| 2004/0096358 A1 | 5/2004 | Blankenstein et al. |
| 2004/0115094 A1 | 6/2004 | Gumbrecht et al. |
| 2004/0228771 A1 | 11/2004 | Zhou et al. |
| 2005/0118073 A1 | 6/2005 | Facer et al. |
| 2005/0161669 A1 | 7/2005 | Jovanovich et al. |
| 2005/0221281 A1 | 10/2005 | Ho |
| 2005/0238545 A1 | 10/2005 | Parce et al. |
| 2005/0243304 A1 | 11/2005 | Padmanabhan et al. |
| 2005/0255003 A1 | 11/2005 | Summersgill et al. |
| 2006/0002827 A1 | 1/2006 | Curcio et al. |
| 2006/0094119 A1 | 5/2006 | Ismagilov et al. |
| 2006/0108012 A1 | 5/2006 | Barrow et al. |
| 2006/0246526 A1 | 11/2006 | Inganas et al. |
| 2006/0257992 A1 | 11/2006 | McDevitt et al. |
| 2006/0275852 A1 | 12/2006 | Montagu |
| 2007/0048189 A1 | 3/2007 | Cox et al. |
| 2007/0298433 A1 | 12/2007 | Sia et al. |
| 2008/0085219 A1 | 4/2008 | Beebe et al. |
| 2008/0110500 A1 | 5/2008 | Kido et al. |
| 2008/0248590 A1 | 10/2008 | Gulliksen et al. |

(56) References Cited

U.S. PATENT DOCUMENTS

| | | |
|---|---|---|
| 2010/0158756 A1 | 6/2010 | Linder et al. |
| 2010/0196207 A1 | 8/2010 | Steinmiller et al. |
| 2012/0269701 A1 | 10/2012 | Linder et al. |
| 2013/0236375 A1 | 9/2013 | Tan et al. |
| 2015/0251178 A1 | 9/2015 | Tan et al. |

FOREIGN PATENT DOCUMENTS

| | | |
|---|---|---|
| EP | 1 054 259 A1 | 11/2000 |
| EP | 1946830 A1 | 7/2008 |
| EP | 2071026 A1 | 6/2009 |
| JP | H10-26625 A | 1/1998 |
| JP | 2007-232172 A | 9/2007 |
| WO | WO 91/01003 A | 1/1991 |
| WO | WO 00/20785 A1 | 4/2000 |
| WO | WO 02/22250 A2 | 3/2002 |
| WO | WO 03/054513 A2 | 7/2003 |
| WO | WO 04/087951 A3 | 10/2004 |
| WO | WO 2005/056186 A1 | 6/2005 |
| WO | WO 2005/072858 A1 | 8/2005 |
| WO | WO 2006/018044 A1 | 2/2006 |
| WO | WO 2006/056787 A1 | 6/2006 |
| WO | WO 2006/113727 A2 | 10/2006 |
| WO | WO 2007/039717 A1 | 4/2007 |
| WO | WO 2008/118098 A1 | 10/2008 |
| WO | WO 2008/123112 A1 | 10/2008 |
| WO | WO 2011/066361 A1 | 6/2011 |
| WO | WO 2011/130629 A1 | 10/2011 |

OTHER PUBLICATIONS

International Preliminary Report on Patentability for PCT/US2010/057969 dated Jun. 7, 2012.

International Search Report and Written Opinion for PCT/US2011/032685 dated Sep. 23, 2011.

Ahn et al., Disposable Smart Lab on a Chip for Point-of-Care Clinical Diagnostics. Proceedings of the IEEE. 2004; 92(1):154-73.

Andersson et al., Micromachined Flow-Through Filter-Chamber for Chemical Reactions on Beads. Sensors and Actuators. 2000;B67:203-8.

Atencia et al., Capillary Inserts in Microcirculatory Systems. Lab Chip. 2006;6:575-7.

Atencia et al., Steady Flow Generation in Microcirculatory Systems. Lab Chip. 2006;6:567-74.

Daridon et al., Chemical Sensing Using an Integrated Microfluidic System Based on the Berthelot Reaction. Sensors and Actuators B. 2001;76:235-43.

Dodge et al., Electrokinetically Driven Microfluidic Chips with Surface-Modified Chambers for Heterogeneous Immunoassays. Anal Chem. 2001;73:3400-9.

Fredrickson et al., Macro-to-Micro Interfaces for Microfluidic Devices. Lab Chip. 2004;4:526-33.

Grodzinski et al., A Modular Microfluidic System for Cell Pre-Concentration and Genetic Sample Preparation. Biomedical Microdevices. 2003;5(4):303-10.

Hosokawa et al. Droplet-Based Nano/Picoliter Mixer Using Hydrophobic Microcapillary Vent. Micro Electro Mechanical Systems. Conference in Orlando, Florida. Jan. 17-21, 1999:388-93.

Juncker et al., Autonomous Microfluidic Capillary Systems. Anal. Chem. 2002;74:6139-44.

Linder et al., Reagent-Loaded Cartridges for Valveless and Automated Fluid Delivery in Microfluidic Devices. Anal Chem. 2005;77(1):64-71.

Moorthy et al., Microfluidic Tectonics Platform: A Colorimetric, Disposable Botulinum Toxin Enzyme-Linked Immunosorbent Assay System. Electrophoresis. 2004;25:1705-13.

Obeid et al., Microfabricated Device for DNA and RNA Amplification by Continuous-Flow Polymerase Chain Reaction and Reverse Transcription-Polymerase Chain Reaction with Cycle Number Selection. Anal Chem. 2003;75:288-95.

Proceedings of uTAS 2004, 8th International Conference on Miniaturized Systems in Chemistry and Life Sciences, Sep. 26-30, Malmo, Sweden, Edited by Thomas Laurell, Johan Nilsson, Klavs Jensen, D. Jed Harrison, Jorg P. Kutter, The Royal Society of Chemistry, pp. 1-135 (2004).

Sia et al., An Integrated Approach to a Portable and Low-Cost Immunoassay for Resource-Poor Settings. Angew. Chem. Int. Ed. 2004;43:498-502.

Sia et al., Microfluidic Devices Fabricated in Poly(Dimethlysiloxane) for Biological Studies. Electrophoresis. 2003;24:3563-76.

Song et al., A Microfluidic System for Controlling Reaction Networks in Time. Angew Chem Int Ed. 2003;42(7):768-72.

Weigl et al., Lab-on-a-Chip for Drug Development. Advanced Drug Delivery Reviews. 2003;55:349-77.

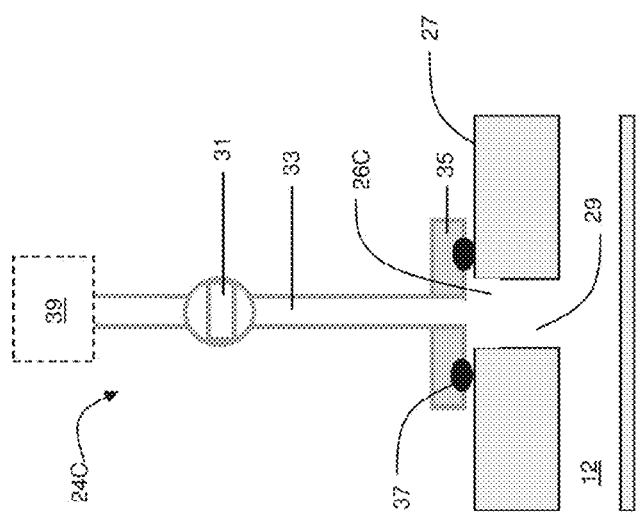
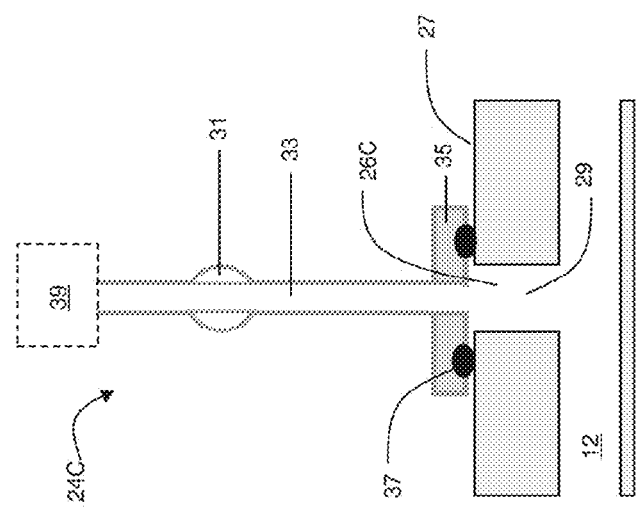

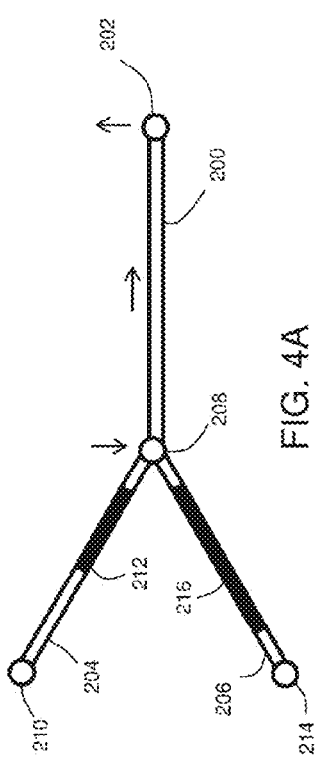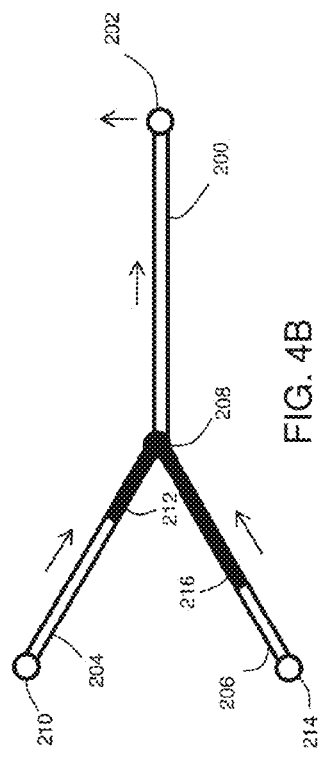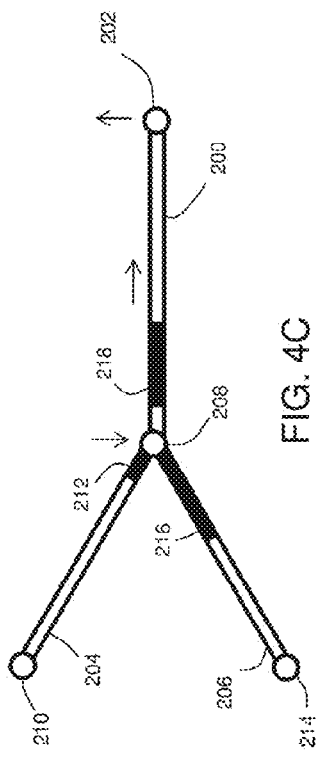

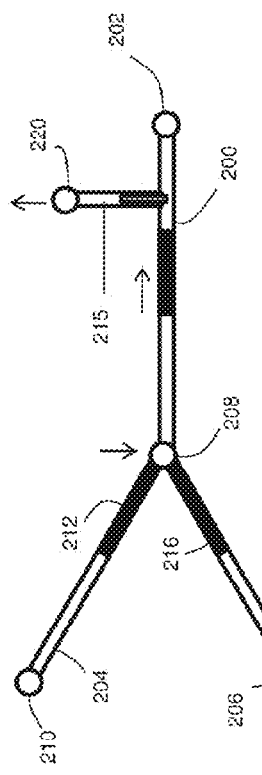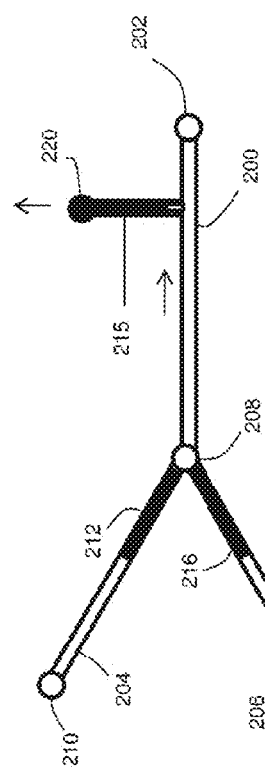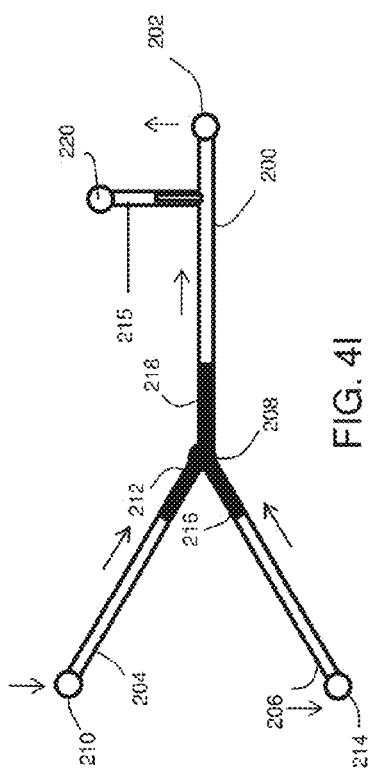

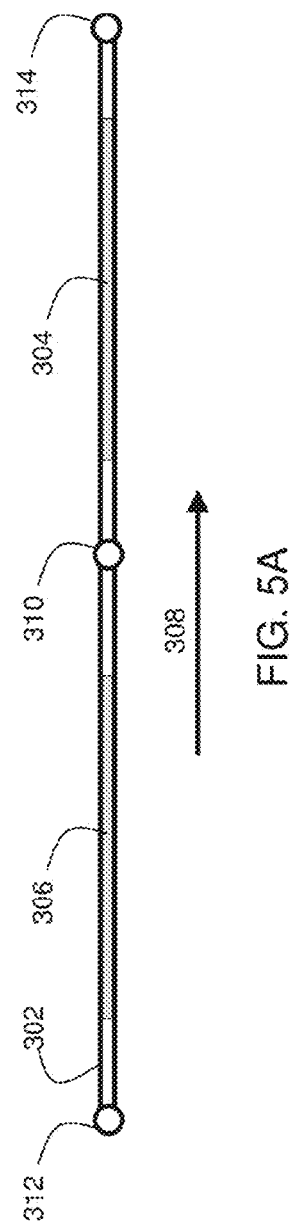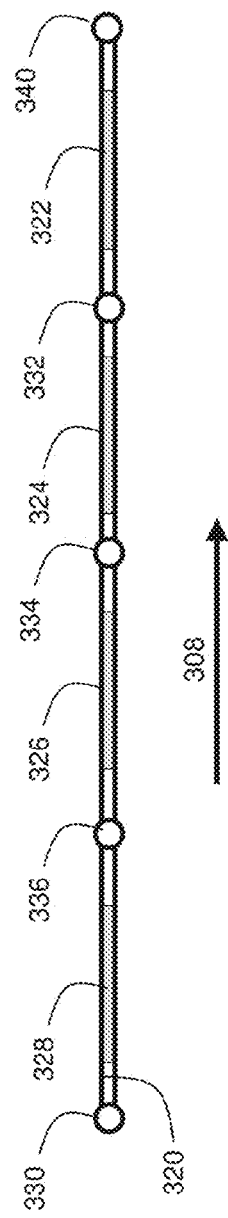

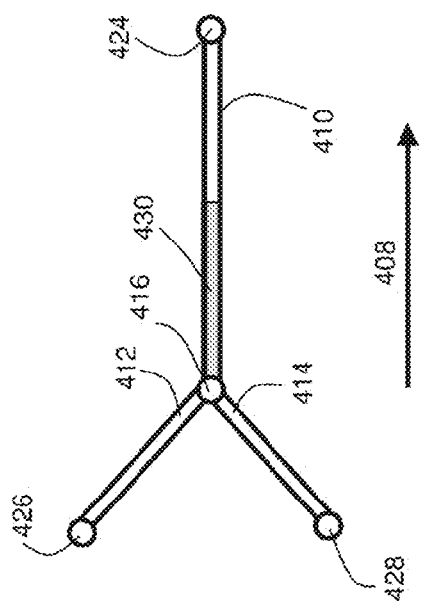
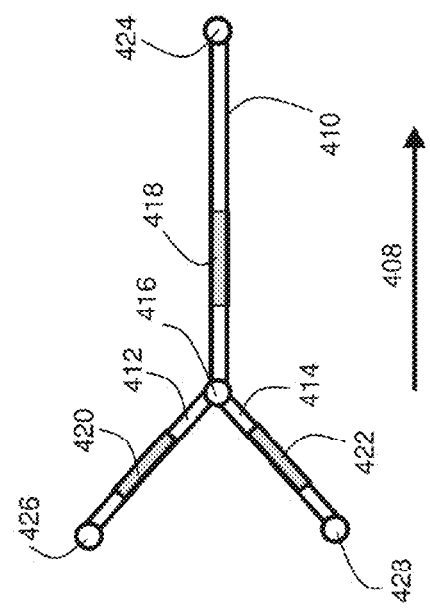
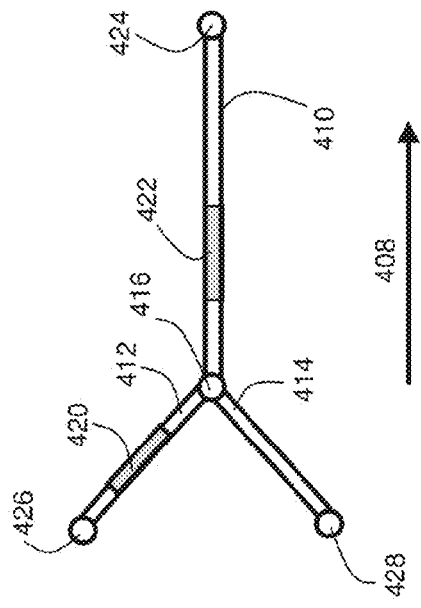

FLUID MIXING AND DELIVERY IN MICROFLUIDIC SYSTEMS

RELATED APPLICATIONS

The present application is a continuation of U.S. Ser. No. 14/521,959, filed Oct. 23, 2014, which is a continuation of U.S. Ser. No. 14/039,786, filed Sep. 27, 2013, which is a continuation of U.S. Ser. No. 12/953,771, filed Nov. 24, 2010 and issued as U.S. Pat. No. 8,567,425 on Oct. 29, 2013, which claims priority under 35 U.S.C. §119(e) to U.S. provisional patent application, U.S. Ser. No. 61/263,981, filed Nov. 24, 2009, each of which is incorporated herein by reference.

FIELD OF INVENTION

Systems and methods for mixing and delivering fluids in microfluidic systems are generally described. In some cases, the fluids contain reagents that can participate in one or more chemical or biological reactions.

BACKGROUND

The manipulation of fluids plays an important role in fields such as chemistry, microbiology and biochemistry. These fluids may include liquids or gases and may provide reagents, solvents, reactants, or rinses to chemical or biological processes. While various microfluidic methods and devices, such as microfluidic assays, can provide inexpensive, sensitive and accurate analytical platforms, fluid manipulations—such as the mixture of multiple fluids, sample introduction, introduction of reagents, storage of reagents, separation of fluids, collection of waste, extraction of fluids for off-chip analysis, and transfer of fluids from one chip to the next—can add a level of cost and sophistication. Accordingly, advances in the field that could reduce costs, simplify use, and/or improve fluid manipulations in microfluidic systems would be beneficial.

SUMMARY OF THE INVENTION

Systems and methods for mixing and delivering fluids in microfluidic systems are generally described. The subject matter of the present invention involves, in some cases, interrelated products, alternative solutions to a particular problem, and/or a plurality of different uses of one or more systems and/or articles.

In one set of embodiments, a series of methods are provided. In one embodiment, a method comprises providing a device comprising a main channel, a first branching channel containing a first fluid, a second branching channel containing a second fluid, wherein the first and second branching channels connect at an intersection and are fluidically connected to the main channel, and a vent valve positioned between a portion of the first branching channel and a portion of the main channel. The method involves actuating the vent valve, causing the first and second fluids to flow into the intersection substantially simultaneously, and mixing at least portions of the first and second fluids to produce a mixed fluid.

In another embodiment, a method comprises providing a device comprising an upstream channel portion containing a first fluid, a downstream channel portion containing a second fluid different from the first fluid, and a vent valve positioned between the upstream and downstream channel portions. While the first and second channel portions are in fluid communication with one another, the second fluid is flowed in the downstream channel portion without substantially flowing the first fluid. The method also includes flowing the second fluid from the upstream channel portion to the downstream channel portion after the flowing of the first fluid.

In another set of embodiments, a series of devices are provided. In one embodiment, a device comprises an inlet, an outlet, an upstream channel portion in fluid communication with the inlet, a downstream channel portion in fluid communication with the outlet, and a vent valve positioned between the downstream and upstream channel portions. A first fluid is stored in at least one of the upstream and downstream channel portions, and the device is sealed and constructed and arranged for storing the first fluid in the device for at least one hour prior to first use.

In another embodiment, a device comprises an inlet, an outlet, a main channel between the inlet and the outlet, and a first and a second vent valve positioned in series along the main channel between the inlet and the outlet.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 2A-2F include, according to one set of embodiments, cross-sectional schematic illustrations of vent valves that can be used in devices described herein;

FIGS. 4A-4I include schematic diagrams of branched channels, according to one set of embodiments;

FIGS. 5A-5B include schematic illustrations of fluid plugs in a channel of a device, according to one set of embodiments;

FIGS. 6A-6C include exemplary schematic illustrations of various arrangements of fluid plugs in channels of a device, according to one set of embodiments;

DETAILED DESCRIPTION

Figure 1:
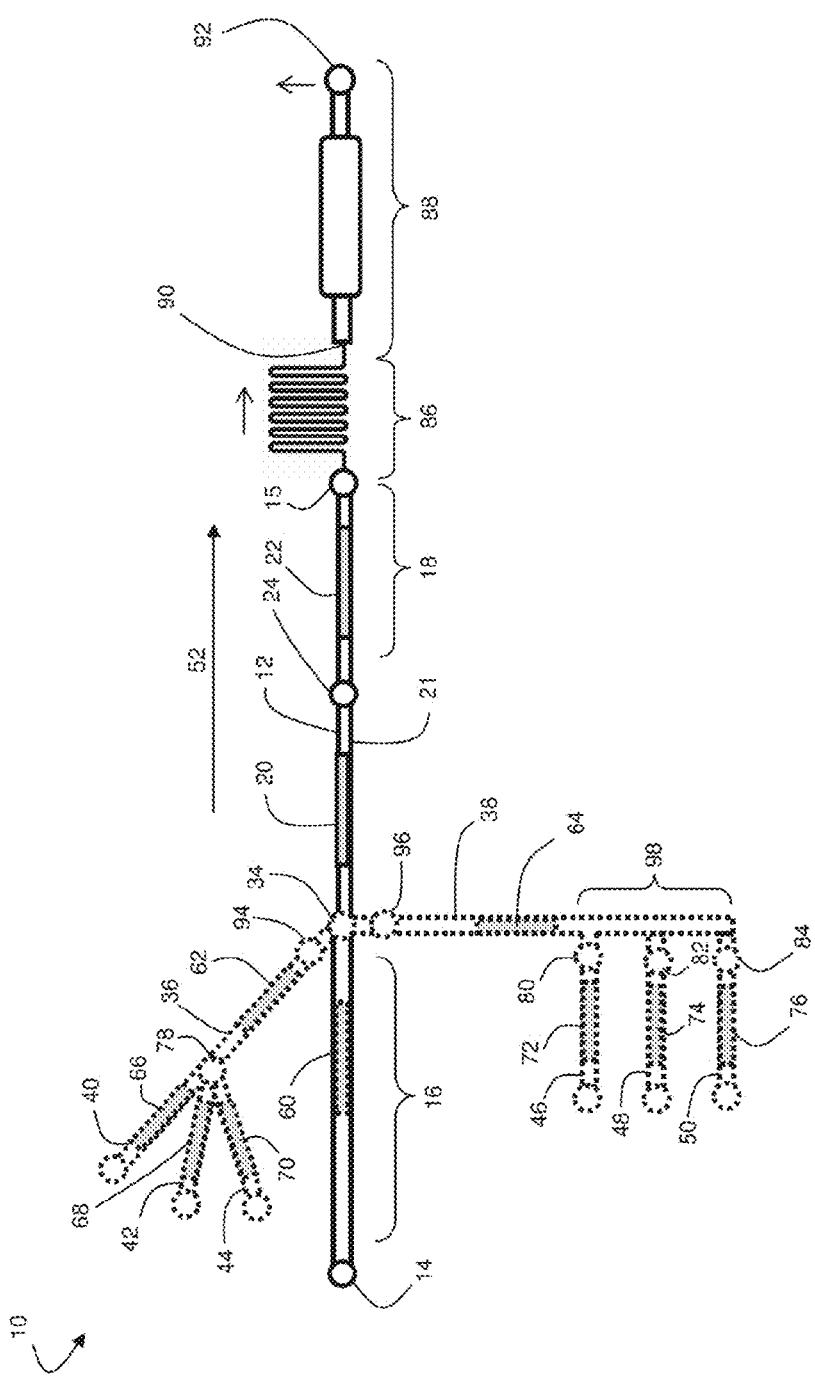
FIG. 1 includes a schematic illustration of a device including a plurality of vent valves, according to one set of embodiments.

The specification generally discloses systems and methods for mixing and delivering fluids in microfluidic systems. The fluids can contain, in some embodiments, reagents that can participate in one or more chemical or biological reactions. Some embodiments relate to systems and methods employing one or more vent valves to controllably flow and/or mix portions of fluid within a microfluidic system. The vent valves can comprise, for example, a port in fluid communication with the microfluidic channel in which a fluid is positioned, and may be actuated by positioning a seal over the port opening or by removing the seal from the port opening. In certain embodiments, the seal may include a valving mechanism such as a mechanical valve operatively associated with a tube in fluid communication with the port. Generally, opening the vent valve allows the port to function as a vent. When the port functions as a vent, the fluid located on one side of the vent valve flows, while the fluid located on the opposite side of the vent valve relative to the first fluid remains stationary. When the valve is closed, the port no longer functions as a vent, and the fluid located on both sides of the vent valve can flow through the system towards an outlet. Advantageously, fluid control such as a sequence of fluid flow and/or a change in flow rate, can be achieved by opening and closing one or more vent valves and by applying a single source of fluid flow (e.g., a vacuum) operated at a substantially constant pressure. This can simplify the operation and use of the device by an intended user.

Vent valves can be actuated so as to control the movement of fluid in the microfluidic system. For example, fluids can be stored serially in a channel, and after closing a vent valve positioned along the channel, the fluids can flow sequentially towards the channel outlet. In some cases, fluids can be stored in separate, intersecting channels, and after closing a vent valve the fluids will flow together toward a point of intersection. This set of embodiments can be used, for example, to controllably mix the fluids as they flow together. The timing of delivery and the volume of fluid delivered can be controlled, for example, by the timing of the vent valve actuation.

Advantageously, the vent valves described herein can be operated without constricting the cross-section of the microfluidic channel on which they operate, as might occur with certain valves in the prior art. Such a mode of operation can be effective in preventing leaking across the valve. Moreover, because vent valves can be used, some systems and methods described herein do not require the use of certain internal valves, which can be problematic due to, for example, their high expense, complexity in fabrication, fragility, limited compatibility with mixed gas and liquid systems, and/or unreliability in microfluidic systems. By using an external valve such as a vent valve, macro-scale (rather than micro-scale) mechanical features are employed, which are generally less expensive to fabricate and more robust in operation. In addition, the external valves described herein function well with heterogeneous fluids (e.g., gas/liquid combinations) and fluids containing bubbles, droplets, and/or particles.

In certain embodiments, the fluids used in the systems described herein can be stored within the systems themselves. While external valves may control the timing of reagent delivery, injection of liquid reagents is not required to operate some such systems. The ability to operate the systems without making external connections to fluid sources can greatly simplify operation.

The articles and systems described herein may be produced inexpensively and, in some cases, may be disposable. In addition, the articles and systems described herein can be fabricated quickly due to the absence of complex mechanical features, in some embodiments. These advantages can allow one to test and implement a wide range of configurations, which may be suitable for a large number of chemical and biological systems (e.g., biological assays). Other advantages are described in more detail below.

The systems and methods described herein may find application in a variety of fields. In some cases, the systems and methods can be used to control fluid flow and mixing in a variety of microfluidic systems such as, for example, microfluidic point-of-care diagnostic platforms, microfluidic laboratory chemical analysis systems, fluidic control systems in cell cultures or bio-reactors, among others. The articles, systems, and methods described herein may be particularly useful, in some cases, wherein an inexpensive, robust, disposable microfluidic device is desired. The fluid control described herein may be used to perform any suitable chemical and/or biological reaction. As a specific example, the fluid control described herein may be used to control reagent transport in antibody assays that employ unstable reaction precursors, such as the silver solution assay described in the Examples section.

The articles, components, systems, and methods described herein may be combined with those described in International Patent Publication No. WO2005/066613 (International Patent Application Serial No. PCT/US2004/043585), filed Dec. 20, 2004 and entitled "Assay Device and Method"; International Patent Publication No. WO2005/072858 (International Patent Application Serial No. PCT/US2005/003514), filed Jan. 26, 2005 and entitled "Fluid Delivery System and Method"; International Patent Publication No. WO2006/113727 (International Patent Application Serial No. PCT/US06/14583), filed Apr. 19, 2006 and entitled "Fluidic Structures Including Meandering and Wide Channels"; U.S. patent application Ser. No. 12/113,503, filed May 1, 2008 and entitled "Fluidic Connectors and Microfluidic Systems" and published as U.S. Publication No. 2008/0273918; U.S. patent application Ser. No. 12/196,392, filed Aug. 22, 2008, entitled "Liquid containment for integrated assays" and published as U.S. Publication No. 2009/0075390; U.S. patent application Ser. No. 12/428,372, filed Apr. 22, 2009, entitled "Flow Control in Microfluidic Systems" and published as U.S. Publication No. 2009/0266421; U.S. patent application Ser. No. 12/640,420, filed Dec. 17, 2009, entitled, "Reagent Storage in Microfluidic Systems and Related Articles and Methods" and published as U.S. Publication No. 2010/0158756; and U.S. patent application Ser. No. 12/698,451, filed Feb. 2, 2010, entitled, "Structures for Controlling Light Interaction with Microfluidic Devices" and published as U.S. Publication No. 2010/0196207; U.S. patent application Ser. No. 61/325,023, filed Apr. 16, 2010, entitled, "Feedback Control in Microfluidic Systems"; U.S. patent application Ser. No. 61/325,044, filed Apr. 16, 2010, entitled, "System for Analysis of Samples"; and U.S. patent application Ser. No. 60/363,002, filed Jul. 9, 2010, entitled, "Systems and Devices for Analysis of Samples", each of which is incorporated herein by reference in its entirety for all purposes.

A series of exemplary devices including vent valves and other components are now described.

FIG. 1 includes an exemplary schematic illustration of a device comprising one or more vent valves and one or more fluids, according to one set of embodiments. In the set of embodiments illustrated in FIG. 1, a device 10 includes a channel 12 comprising an inlet 14, an outlet 15, an upstream portion 16, and a downstream portion 18. The channel can also contain a fluid in at least one of the upstream and downstream channel portions, such as a first fluid 20. The channel can also contain, in addition to or in place of the first fluid, a second fluid 22. In embodiments in which multiple fluids are stored, the fluids can be separated from one another by one or more immiscible separating fluid plugs (e.g., a separation fluid such as a gas (e.g., air) or an oil). In some instances, the device (including any inlets, outlets, and vent valves) is sealed and is constructed and arranged for storing a fluid (e.g., either or both of fluids 20 and 22) in the device prior to first use of the device by an intended user.

As shown illustratively in FIG. 1, first fluid 20 and second fluid 22 are not in direct contact with each other. For example, the first and second fluids within the channel may be separated by a third fluid 21 that is immiscible with both the first and second fluids. In one set of embodiments, fluids 20 and 22 can both be liquids separated by, for example, a plug of gas positioned between them. In another embodiment, fluids 20 and 22 are liquids separated by a third liquid that is immiscible with both liquids. When more than two fluids are employed, any suitable combination of gases and liquids can be used to separate multiple portions of fluid within the channel(s).

Device 10 also comprises a vent valve 24 positioned between the downstream and upstream channel portions. As used herein, a "vent valve" refers to a valve that comprises a port in fluid communication with a channel, and a mechanism that can be operated to open and close the port, wherein the vent valve exposes the channel interior to, or seals the channel interior from, an environment external to the channel interior. Exemplary exterior environments can include, for example, an ambient environment (e.g., air) and a reservoir containing a fluid (e.g., a pressurized or unpressurized gas).

Figure 2A:
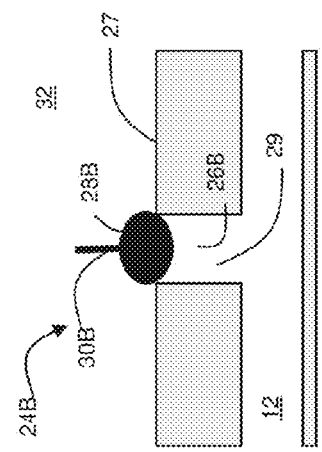
Figure 2B:
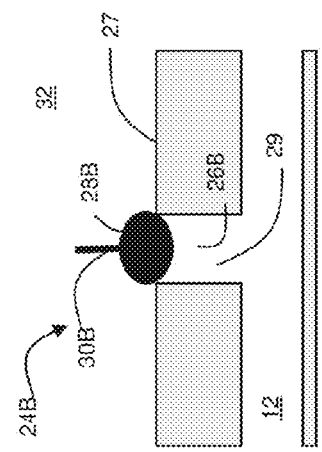
Figure 2C:
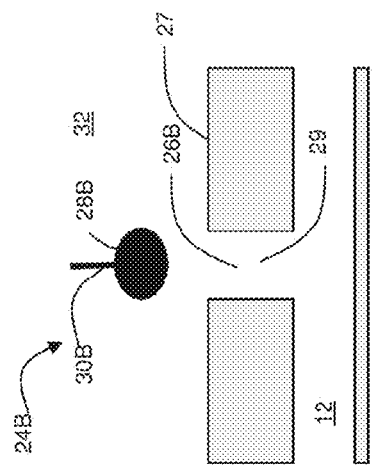
Figure 2D:
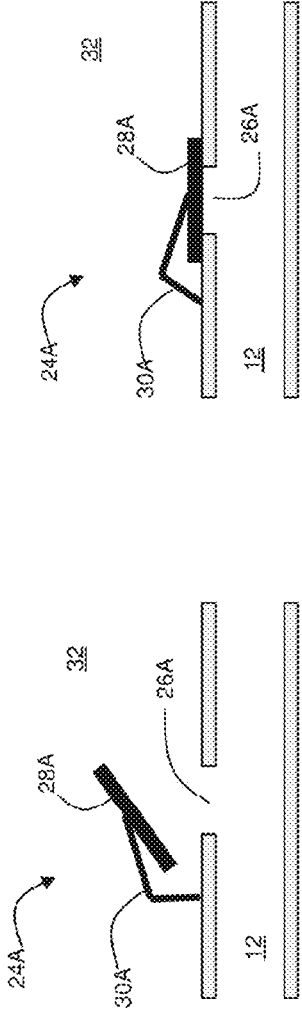

FIGS. 2A-2F include exemplary cross-sectional schematic illustrations of a vent valve. In the set of embodiments illustrated in FIGS. 2A-2B, vent valve 24A is positioned adjacent channel 12. The vent valve includes a port 26A in fluid communication with the channel. In addition, the vent valve includes a seal 28A (e.g., a cover) which can be moved by an actuator 30A. In FIG. 2A, the vent valve is open such that channel 12 is exposed to an ambient environment 32 via port 26A. In FIG. 2B, the vent valve is closed such that channel 12 is isolated from ambient environment 32 by seal 28A. As shown in the illustrative embodiments of FIGS. 2C-2D, vent valve 24B includes a seal 28B in the form of a plug that can block an opening of port 26B. Seal 28B may be deformable in some embodiments.

As shown in the illustrative embodiments of FIGS. 2E-2F, vent valve 24C includes a valving mechanism 31 operatively associated with a tube 33 defining a channel (e.g., a microfluidic channel) permitting fluid flow. The tube is attached to a plate 35 which, when pressed against the microfluidic substrate (e.g., exterior surface 27), may form a fluid-tight seal. The seal may be formed using a compressed gasket or o-ring 37, or any other suitable component as described in more detail below. Alternatively, the tube may be press-fit into the port. As shown in FIGS. 2E-2F, the valve is in fluidic communication with port 26C. The valve can be opened or closed by actuating valving mechanism 31. When the valve is open, e.g., as illustrated in FIG. 2E, fluid in tube 33 can freely flow across the valving mechanism. In such and other embodiments, channel 12 is exposed to and in fluid communication with an environment 39 at the other end of the tube. When the valve is closed, e.g., as illustrated in FIG. 2F, fluid in tube 33 can no longer flow across the valving mechanism; therefore, channel 12 is isolated from and no longer in fluid communication with environment 39 at the other end of the tube. It should be appreciated that environment 39 may be any suitable environment, including an ambient environment (e.g., the tube can be open to air) and a reservoir containing a fluid (e.g., a gas such as compressed air or nitrogen).

One of ordinary skill in the art would be capable of selecting a suitable actuation mechanism and/or seal to be used for a specific application. Non-limiting examples of a valving mechanism which may be operatively associated with a tube or other suitable component of a vent valve include a diaphragm valve, ball valve, gate valve, butterfly valve, globe valve, needle valve, pinch valve, poppet valve, or pinch valve. The valving mechanism may be actuated by any suitable means, including a solenoid, a motor, by hand, or by hydraulic/pneumatic pressure. Additionally, any suitable seal may be used. In some embodiments, the seal can comprise a rubber or other elastomeric material which can be, in some cases, selected to be compatible with one or more fluids within the system. Suitable seal materials include, but are not limited to, natural rubbers, thermoplastics, synthetic rubbers (e.g., fluoropolymers, neoprene, nitrile, silicone, fluorosilicone, etc.), or combinations of these. The seal can be affixed to or integrally formed on a surface of the vent valve, in some embodiments. In some cases, the seal can comprise a lip (not shown) on a surface of the vent valve designed to engage a corresponding notch on a surface of the device (or vice versa) such that when the vent valve is in a closed position, the lip engages the notch to form a seal.

In some cases, one or more vent valves can be electronically actuated. For example, in some embodiments, a sensor may be in operative association with an actuator and/or a microprocessor able to open or close the vent valve in response to a signal determined within the system. In some cases, a vent valve may be electronically actuated based upon timing dictated, for example, by a pre-determined program executed by a microprocessor. It is to be understood that any suitable control system and technique disclosed herein can potentially be provided in combination with other control systems not specifically described to provide other or additional functionality.

The vent valve can be positioned, in some cases, such that the port is located adjacent (e.g., over) at least a portion of the microfluidic channel. For example, in some embodiments, the port can comprise an opening connecting the channel interior to an exterior surface 27 of the device in which the channel is formed, as illustrated in FIGS. 2A-2B. Although FIGS. 2A-2B show an opening of the port being directly adjacent exterior surface 27, in other embodiments such as those shown in FIGS. 2C-2D, an opening of a port can be connected to a channel interior by an intervening channel 29. In some embodiments, a channel is formed in an article, and the port can be formed such that it extends in a direction that is substantially out of the plane of the article. For example, in some embodiments, the port may be formed by drilling a hole into the top surface of a substrate in which the channel is formed. In other embodiments, the port can be molded into a substrate fabricated by injection molding using a pin located in the mold cavity, e.g., as described in Example 1.

The vent valve can be used to control the movement of fluid within a channel system. Referring back to FIG. 1, a vacuum can be applied to outlet 92 (with outlet 15 closed, or to 15 with outlet 92 closed), which can pull fluid 22 toward the outlet in the direction of arrow 52. When vent valve 24 is open, a fluid from an environment exterior to the channel interior can be drawn through the vent valve, and into the channel. For example, when the fluid in the exterior environment is ambient air, the air can enter into the channel interior upon opening of the vent valve. In some cases, this fluid from the external environment can mix with a fluid inside the channel system. For instance, in embodiments in which fluid 21, which is positioned at vent valve 24, is a gas, the ambient air entering into the channel can mix with fluid 21.

In some cases, such as when the port of the vent valve is in fluid communication with ambient air, the resistance to the flow of fluid 21 or any other fluid adjacent to fluid 20 may be smaller than the resistance to flow of fluid 20 itself, and in such cases fluid 20 can remain substantially stationary inside the channel even when a source of vacuum is applied downstream of fluid 20. This can allow for the flow of fluid 22 through the downstream portion of the channel without substantially flowing fluid 20. When vent valve 24 is closed, ambient air can no longer be drawn into the channel through the vent valve, and fluid 20 is transported through channel 12 in the direction of arrow 52.

In some embodiments, a device described herein includes a plurality of vent valves. A device may comprise, for example, multiple vent valves positioned in series along a main channel between an inlet and an outlet of the main channel. The set of embodiments illustrated in FIG. 1, for example, includes an optional second vent valve 34 that is positioned in series with vent valve 24, between inlet 14 and outlet 15, along channel 12.

In some cases, a device can include one or more branching channels, i.e., channels that intersect with another channel of the device at a point of intersection. For example, in some embodiments, the device comprises a first upstream portion comprising a first branching channel and a second upstream portion comprising a second branching channel. The first and second branching channels can intersect with each other, in some cases. In addition, one or more branching channels can be fluidically connected with a downstream channel portion. In some cases, a device includes one or more branching channels in fluid communication with a main channel, any of which can contain a one or more fluids stored therein (e.g., prior to first use). For example, in the set of embodiments illustrated in FIG. 1, device 10 optionally includes channels 36 and/or 38, which branch from main channel 12. Channels 36 and 38 intersect at the location of optional vent valve 34, and are fluidically connected to the downstream portions of channel 12 (e.g., downstream portion 18). Each of the branching channels can also include branching channels, in some embodiments. For example, any of channels 40, 42, and 44, which branch from channel 36 may be included in the device. In addition, any of channels 46, 48, and 50, which branch from channel 38 may be included in the device in some instances. Optionally, one or more vent valves may be associated with the one or more branching channels. Additional layouts of vent valves and channels, as well as functionalities associated with the same, are described in more detail below.

In one set of embodiments, an upstream channel portion (e.g., of a main channel) can serve as a first branching channel, and the device can further comprise a second branching channel, wherein the first and second branching channels connect at an intersection and are fluidically connected to a downstream channel portion. In the set of embodiments illustrated in FIG. 1, upstream portion 16 of main channel 12 can serve as the first branching channel, while either or both of channels 36 and 38 can serve as second (or third) branching channels.

The channel layouts described herein can be used to store fluids in any suitable configuration. Any of the branching channels can contain one or more fluids in place of or in addition to one or more fluids which may be contained within the main channel. For example, a first fluid can be contained in a main channel, and a second fluid can be contained within a first branching channel. In some cases, a third fluid can be contained in a second branching channel, and so on. For example, in the set of embodiments illustrated in FIG. 1, upstream portion 16 can contain optional fluid 60, optional branching channel 36 can contain optional fluid 62, and optional branching channel 38 can contain optional fluid 64. In addition, optional branching channels 40, 42, and 44 can contain optional fluids, 66, 68, and 70, respectively, and optional branching channels 40, 42, and 44 can contain optional fluids, 72, 74, and 76, respectively. In some cases, one or more of such fluids can be stored and sealed in the device prior to first use.

Vent valves can be positioned in any suitable location within a device. In some cases, vent valves are positioned between two fluids (e.g., two stored fluids). For example, in the set of embodiments illustrated in FIG. 1, vent valve 24 is positioned between first fluid 20 and second fluid 22. Additionally or alternatively, optional vent valve 34 can be positioned between optional third fluid 60, and first fluid 20 and/or second fluid 22. In some cases, a vent valve is positioned between a portion of a first branching channel and a portion of a main channel. For instance, a vent valve can be positioned at the intersection of two or more channels, such as at the intersection of a branching channel and a main channel. For example, in FIG. 1, optional vent valve 34 is positioned at the intersection of channel 12 and optional channels 36 and 38. In addition, optional vent valve 78 is positioned at the intersection of optional channels 40, 42, 44, and 36. In some cases, one or more vent valves can be positioned at a portion of a branching channel. For example, in FIG. 1, branching channels 46, 48, and 50 include vent valves 80, 82, and 84, respectively, which are positioned at non-intersecting portions of the branching channels.

Methods of transporting and/or mixing fluids are also provided. In one set of embodiments, a method comprises causing one or more fluids to move while keeping one or more other fluids substantially stationary. For example, in the set of embodiments illustrated in FIG. 1, a pressure gradient can be applied to channel 12, e.g., by applying a negative pressure to an outlet (e.g., outlet 15 with outlet 92 closed or outlet 92 with outlet 15 closed). When vent valve 24 is in the open position, the pressure gradient can cause fluid 22 to flow through channel 12 in the direction of arrow 52. This can occur without substantially flowing fluid 20 as described herein. In some embodiments, ambient air, having a lower resistance to fluid flow than fluid 20 within channel 12, can be pulled through vent valve 24, allowing fluid 20 to remain substantially stationary. In some embodiments, a second fluid from a portion of the channel upstream of the portion from which the first fluid is flowed can be transported by actuating a vent valve between the upstream and downstream channel portions such that the vent is closed. For example, in FIG. 1, when vent valve 24 is in the closed position and an upstream inlet (e.g., inlet 14) or vent valve (e.g., vent valve 34) is open, the pressure gradient can cause fluid 20 to flow through channel 12 in the direction of arrow 52.

The timing of fluid flow can also be controlled using the systems and methods described herein. For instance, in some embodiments, fluids 22 and 20 can be transported through channel 12 substantially simultaneously (e.g., by applying a vacuum after closing vent valve 24). In other embodiments, fluids 22 and 20 can be transported through channel 12 sequentially (e.g., by first applying a vacuum before closing vent valve 24, thereby transporting fluid 22, and then closing vent valve 24 to transport fluid 20). These methods can be generally used to control the flow of any fluid within any channel by closing appropriate vent valves between the negative pressure source and the fluid one wishes to flow within the channel. For example, if transport of optional fluid 62 is desired, a negative pressure can be applied to outlet 92 while outlet 15 and vent valves 24 34, and 94 are closed (and while a valve upstream of fluid 62, such as vent valve 78 remains open). In some cases, this transport takes place when other branches such as branches 16 and 38 include inlets or vent valves, positioned upstream of any fluid contained in the branches, are in the closed position, or in devices that do not include other branches such as branches 16 and 38. Using these and other methods, fluids can be transported to a desired location (e.g., a reaction site) within a fluidic system at specific and predetermined points in time, and in a particular order, to carry out a reaction or other fluidic process. Furthermore, the articles and methods described herein can allow a first set of processes to be decoupled from a second set of processes. For instance, the time of mixing of two or more fluids within one or more mixing regions can be decoupled from the time of incubation of a sample within a reaction area, as each of these processes can be controlled independently. Further advantages and examples are provided herein.

Methods of mixing two or more fluids are also provided. Mixing may involve the use of branching channels in some cases. In some embodiments, a method comprises providing a device with a main channel, a first branching channel containing a first fluid, and a second branching channel containing a second fluid, wherein the first and second branching channels connect at an intersection and are fluidically connected to the main channel. In some embodiments, the first branching channel can include a portion of a main channel that is upstream of the intersection. For example, in the set of embodiments illustrated in FIG. 1, the main channel can comprise channel 12, while the first branching channel can comprise upstream portion 16 (containing fluid 60), and the second branching channel can comprise channel 36 (containing fluid 62). In some cases, the first and second branching channels both deviate in direction from the main channel. For example, in FIG. 1, the main channel can comprise channel 12, with the first branching channel comprising channel 36 (containing fluid 62), and the second branching channel comprising channel 38 (containing fluid 64). In some embodiments, the device can include a vent valve positioned between a portion of the first branching channel and a portion of the main channel. In some cases, the vent valve can be positioned at the intersection of the first and second branching channels. For example, in FIG. 1, vent valve 34 is positioned at the intersection of channels 12, 38, and 36. In some embodiments, the vent valve can be positioned upstream from an intersection of the branching channels. For example, in FIG. 1, optional vent valve 94 is positioned over channel 36, upstream of the intersection of channels 36 and 38. In some instances, the device can include a vent valve positioned between a portion of the second branching channel and a portion of the main channel. In FIG. 1, vent valve 34 is positioned between second branching channel 38 and main channel 12. In addition, optional vent valve 96 is positioned between a portion of second channel 38 and main channel 12.

In some embodiments, a method of mixing can comprise actuating at least one vent valve while providing a pressure gradient across two openings in the device (e.g., an inlet and an outlet) to cause first and second fluids to flow into an intersection of two or more channels. The flow of the first and second fluid into the intersection may occur substantially simultaneously. In some cases, at least a portion of each of the fluids transported to the intersection can be mixed to produce a mixed fluid. A single vent valve can be actuated to cause the flow of two or more fluids. For example, in FIG. 1, when vent valve 34 is closed (and optional vent valves 94 and 96 are absent) two or more of fluids 62, 60, and 64 can be flowed toward the intersection of channels 12, 36, and/or 38, as long as at least one inlet or vent valve upstream of each of these fluids are open. As another example, when optional vent valve 78 is closed (assuming other vent valves between valve 78 and the pressure gradient source are also closed) two or more of fluids 66, 68, and 70 can be transported to the intersection of channels 40, 42, and/or 44 as long as at least one inlet or vent valve upstream of each of these fluids are open.

In some embodiments, a device may include a main channel, a first branching channel containing a first fluid, a second branching channel containing a second fluid, wherein the first and second branching channels connect at an intersection and are fluidically connected to the main channel. A third fluid may optionally be provided in the main channel, which may be, for example, downstream of the branching channels. A vent valve may be positioned between a portion of the first branching channel and a portion of the main channel (e.g., at the intersection of the first and second channels, or along the main channel). Operating the system may involve actuating the vent valve, causing the first and second fluids to flow into the intersection substantially simultaneously, and mixing at least portions of the first and second fluids to produce a mixed fluid. In some embodiments, the third fluid in the main channel may be flowed before actuating the vent valve (or a series of vent valves) without substantially flowing the first and second fluids. After the third fluid is flowed in the main channel (e.g., towards a reaction site or other portion of the device), the vent valve that is positioned between a portion of the first branching channel and a portion of the main channel may be actuated to allow the flow of the first and second fluids as described above. In some instances, a substantially constant vacuum is applied at the outlet of the main channel and timing of the flow of the third, second, and first fluids is accomplished by timing of actuation of the vent valve. Operating the system may include, in some cases, waiting a predetermined time after actuating the vent valve in order to allow for a predetermined amount of mixing (e.g., such that not all of the first and second fluids are allowed to combine), and then opening the vent valve to stop the flow of the remaining first and second fluids in the first and second branching channels, respectively, from flowing into the main channel. Accordingly, a predetermined mixed amount of the first and second fluids may be delivered to the main channel using this method of timing.

In some embodiments, multiple vent valves are actuated to cause the flow of two or more fluids toward a channel intersection. For example, in FIG. 1, vent valves 94 and 96 can both be closed (e.g., substantially simultaneously), which can cause fluids 62 and 64 to flow toward the intersection of channels 36 and 38 (e.g., substantially simultaneously). Inlet 14, if present, can also remain closed. The fluids may flow due to the presence of a pressure gradient, which may be formed by, for example, applying a substantially constant reduced pressure at outlet 92, and keeping all other inlets, outlets or vent valves between the fluids and outlet 92 closed. In addition, vent valves 80, 82, and 84 can be closed (e.g., substantially simultaneously) to cause fluids 72, 74, and 76 to flow toward portion 98 of channel 38 (e.g., substantially simultaneously). In certain embodiments, the fluids reach a common region (e.g., an intersection, a mixing region, etc.) substantially simultaneously. Substantially simultaneous transport and/or delivery of two or more fluids to a common region can be useful in achieving efficient mixing of the two fluids, for example, by maximizing the common surface area between two or more fluids. In addition, substantially simultaneous delivery of two or more fluids to a common region can aid in delivering substantially equivalent volumes of two or more fluids, as is discussed in more detail below. This can be important in processes that require the mixing of precise volumes of fluid. In some cases, substantially simultaneous delivery of two or more fluids to a common region helps to avoid the formation of bubbles between the mixed fluid and other fluids within the system, as described in more detail below.

One or more parameters of a device can be chosen, in some cases, such that two or more fluids transported through a device contact each other within a region of the device substantially simultaneously. For example, in some cases, the cross-sectional areas of at least two channels (e.g., two branching channels, a branching channel and a main channel, etc.), the viscosities of the fluids to be mixed, the relative volumes of the fluids to be mixed, the linear lengths of the channels containing the fluids to be mixed, the amount of pressures applied, and the distances from each of the fluids to the point of intersection are selected such that, when equal pressures are applied to each of the two channels, the fluids within them flow into an intersection or other common region substantially simultaneously.

In order to control mixing within the system, it may be useful to control the flow rates of the fluids in the system. Problems can arise, for example, if one fluid (e.g., fluid 62 in FIG. 1) reaches a common area such as a vent valve before another fluid (e.g., fluid 60 in FIG. 1). In such cases, mixing might not occur as anticipated. For example, in some cases, the first fluid (e.g., fluid 62), upon reaching vent valve 34 before a second fluid (e.g., fluid 60), can fill the vent valve and effectively trap a bubble of a separating fluid plug between the vent valve and the front end of the second fluid. In this case, a portion of fluid 62 will be separated and flowed down the main channel without mixing with fluid 60. In some embodiments, this can lead to exposing the reaction area or other area of analysis to a first volume of an unmixed reagent (e.g., a reagent in fluid 62), followed by a segment of a separating fluid plug, followed by a substantially irreproducible mixture of fluids 60 and 62. In some such cases, the resulting chemical or biological reaction in the reaction area may be irreproducible.

Without wishing to be bound by theory, the inventors believe that the following theory can be used to better understand the relationship between flow rate, channel dimensions, and viscosities of fluids flowing in a channel system. Laminar flow of an incompressible uniform viscous fluid (e.g., Newtonian fluid) in a tube driven by pressure can be described by Poiseuille's Law, which is expressed as follows:

$$Q = \frac{\pi R^4}{8\eta} \cdot \frac{\Delta P}{L} \qquad \text{(Equation 1)}$$

where Q is the volumetric flow rate (in m³/s, for example), R is the radius in of the tube (m), $\Delta P$ is the change in pressure across the tube (Pa), $\eta$ is the dynamic fluid viscosity (Pa·s), and L is the length of the tube (m). To generalize beyond circular tubes to any closed channel, this equation can be expressed as:

$$Q = \frac{A R_H^2}{8\eta} \cdot \frac{\Delta P}{L} \qquad \text{(Equation 1b)}$$

where A is the cross-sectional area of the channel and $R_H$ is the hydraulic radius, $R_H = 2A/P$ with P being the parameter of the channel. For a circular tube, $AR_H^2 = \pi R^4$. For a rectangular channel of width w and depth d, $AR_H^2 = (wd)^3/(w+d)^2$. When performing a controlled mixing of multiple fluids, it is important to consider the factors impacting the flow of each individual fluid. In a system designed such that the $\Delta P$, $\eta$, $R_H^2$ and L are equal, both fluids should flow in a similar manner and reproducible mixing of the fluid should be achievable. When one or some of these parameters differ for the fluids, the design of the system should be such that the differences cancel out.

In some embodiments two or more fluids that are to be mixed have substantially equivalent volumes. The two or more fluids may also have similar viscosities, and may be positioned in channels having similar channel cross-sections. In some cases, the volume of one or more separating fluid plugs between the front interfaces of the fluids to be mixed and the intersection (e.g., mixing chamber) in which they are to be mixed can be similar for both reagents. This can help ensure that when the fluids begin moving toward an intersection, the fluids reach the intersection substantially simultaneously. These and other parameters may allow the two or more fluids to be delivered to a common area substantially simultaneously, thereby resulting in reproducible mixing.

In some embodiments in which a first fluid has a first volume, and a second fluid has a second volume different than the first volume, the speed of the smaller volume fluid may increase relative to the larger volume fluid, due to the relatively smaller resistance to fluid flow exhibited by the relatively smaller volume fluid (the hydrodynamic resistance to flow for liquids scales as 1/L, L being the length of the fluid segment; assuming equal channel dimensions and viscosities, the shorter fluid segment will flow faster than the longer fluid segment). This can lead to a deviation from a desired mixing ratio, since it may result in a relatively large amount of the smaller volume fluid being added, relative to the larger volume fluid. This behavior can be self-amplifying, because as the smaller volume fluid moves faster its volume is disproportionately decreased, leading to a further increase in speed. To overcome this potential problem, the cross sections of the channels can be selected, or the viscosities of the fluids to be mixed can be selected, so that there is equal resistance to fluid flow in the channels. For instance, to increase the resistance to flow of the smaller volume fluid, the smaller volume fluid may be positioned in a channel having a smaller cross-section than that containing the larger volume fluid in order to match the overall resistance of the larger volume fluid. Additionally or alternatively, the viscosity of the smaller volume fluid may be increased to increase its resistance to fluid flow to match the overall resistance of the larger volume fluid.

In some cases, the transport and/or mixing of fluids within a channel can be enhanced by employing a channel with a relatively small amount of surface roughness. Inhomogeneities in the surface of a channel (e.g., changes in roughness, imperfections in channel surfaces, chemical deposits on a channel surface, etc.) between the storage location of each of the liquids and the mixing chamber, can affect the advancement of the interfaces between the fluid portions and the separating fluid plug (and thus, the bulk of the liquids). As such, in some embodiments described herein, a channel surface has a relatively low surface roughness. The surface of a channel may have a root-mean-square (RMS) surface roughness of, for example, less than about 5 µm. In other embodiments, the RMS surface roughness may be less than about 3 µm, less than about 1 µm, less than about 0.8 µm, less than about 0.5 µm, less than about 0.3 µm, or less than about 0.1 µm.

The addition of wetting agents to a fluid can also promote reproducible advancement of a fluid within a channel. The wetting agents can stabilize the interface between the fluid and the separating fluid plug and/or reduce the impact of inhomogeneities on a surface of a channel. In some embodiments, the wetting agent can be selected such that it does not adversely react with one or more components (e.g., a reagent) within a fluid. Examples of suitable wetting agents include, but are not limited to, non-ionic detergents (e.g., poly(ethylene oxide) derivatives like Tween 20 and Triton, fatty alcohols), anionic detergents (e.g., sodium dodecyl sulfate and related detergents with shorter or longer alkane chains such as sodium decyl sulfate or sodium octadecyl sulfate, or fatty acid salts), cationic detergents (e.g., quaternary ammonium cations such as cetyl trimethylammonium bromide), zwitterionic detergents (e.g., dodecyl betaine) and perfluorodetergents (e.g., Capstone FS-10).

Additionally or alternatively, the surface of a channel can be treated with a substance to facilitate inhibition or enhancement of fluid flow (e.g., hydrophobic or hydrophilic reagents).

In some embodiments, unpredictable fluid behavior can be inhibited by employing relatively fast flow rates of the fluids within a channel. The flow rate may depend on factors such as the viscosities of the fluids to be transported, the volumes of the fluids to be transported, the cross sectional areas and/or cross sectional shapes of the channels containing the fluids, the pressure gradient, among other factors. In some cases, at least one fluid within a channel is transported at a linear flow rate of at least about 1 mm/s, at least about 5 mm/s, at least about 10 mm/s, or at least about 15 mm/s, at least about 25 mm/s, or at least about 100 mm/s. The linear flow rate may, in some embodiments, be between about 1 mm/s and about 100 mm/s, between about 5 mm/s and about 100 mm/s, between about 10 mm/s and about 100 mm/s, between about 15 mm/s and about 100 mm/s, between about 1 mm/s and about 25 mm/s, between about 5 mm/s and about 25 mm/s, between about 10 mm/s and about 25 mm/s, or between about 15 mm/s and about 25 mm/s. Different flow rates may be implemented at different points in time depending on the fluid being transported and/or the process to be carried out in a device. For instance, in one set of embodiments it may be desirable for a sample to be flowed through a reaction area relatively slowly (e.g., 0.5 mm s$^{-1}$) during a first step, but for two fluids to mix in a mixing region at a relatively higher flow rate (e.g., 15 mm s$^{-1}$) during a second step. The vent valves and other articles and methods described herein may be used, optionally in combination with the systems and methods described in U.S. patent application Ser. No. 12/428,372, filed Apr. 22, 2009, entitled "Flow Control in Microfluidic Systems" and published as U.S. Publication No. 2009/0266421, which is incorporated herein by reference, to control and implement such flow rates and change in flow rates during operation of the device. Two linear flow rates applied during two different steps of a process carried out in a device may have a difference of, for example, greater than 1×, 5×, 10×, 15×, 20×, 25×, 30×, 40×, or 50×. For example, a relatively high linear flow rate of 15 mm s$^{-1}$ is 30× faster than a relatively slow linear flow rate of 0.5 mm s$^{-1}$. In some cases, such fluid control is achieved using one or more vent valves, optionally even when a source of pressure or reduced pressure (e.g., vacuum) is applied substantially constantly to the device during the one or more steps.

As described herein, the intersection of two or more channels can comprise a mixing region. Such a region can be useful in promoting mixing of multiple fluids that are flowed from multiple channels to the intersection. In some embodiments, the mixing region can have a larger cross-sectional area than either of the first or second (or third, fourth, etc.) channels (e.g., branching channels) that intersect at the mixing region. For example, a mixing region may have an average cross-sectional area that is at least 1.2 times, at least 1.5 times, at least 1.7 times, at least 2 times, at least 3 times, or at least 5 times the average cross-sectional area of the largest channel intersecting the mixing region. A mixing chamber at the intersection comprising a relatively large volume can help, for example, in compensating for a mismatch in the arrival times of two or more fluids at an intersection of two or more channels.

In other embodiments, however, a relatively smaller mixing region may be present in devices described herein. For example, a mixing region may have an average cross-sectional area that is less than 5 times, less than 3 times, less than 2 times, less than 1.7 times, less than 1.5 times, or less than 1.2 times the average cross-sectional area of the largest channel intersecting the mixing region. In some cases the mixing region has an average cross-sectional area that is substantially the same as the average cross-sectional area of the largest channel intersecting the mixing region.

In some cases, the mixing region can comprise a vent valve. For example, the port of a vent valve can provide a volume in which multiple fluids are mixed. In some embodiments, the cross-sectional area, length, or other parameter of a component (e.g., a channel, a vent valve component (e.g., a port), a mixing region, etc.) can be chosen such that a desired mixing result is achieved upon flowing two or more fluids within the component. For example, in some embodiments, the volume of the vent valve (e.g., a port of a vent valve, or an intervening channel of the vent valve connecting a main channel to an opening of the vent valve) can be chosen such that complete mixing of two or more fluids can be achieved (e.g., via diffusion) during their residence time within the vent valve. The volume of the vent valve, including any intervening channels, may be, for example, less than about 50 µL, less than about 20 µL, less than about 10 µL, less than about 5 µL, less than about 3 µL, less than about 1 µL, less than about 0.1 µL, less than about 0.01 µL, less than about 10 nL, or less than about 1 nL. Other volumes are also possible.

In a laminar flow environment (which is common to most microfluidic systems), the mixing of reagents relies mostly on diffusion. In this context, mixing between reagents gradually increases as the reagents flow together along a channel. In such cases, the length of a main channel (e.g., between the vent where mixing occurs and the point of use of the mixed reagents, such as the reaction area) can be chosen such that complete or sufficient mixing of two or more fluids can be achieved (e.g., via diffusion) during their residence time within the channel.

Mixing based on diffusion can also be increased by increasing the combined fluid's residence time in the channel. In some cases, an incubation step can be added to the system. For example, in a system with a substantially constant vacuum applied at outlet 92, and having combined two liquids upstream of vent valve 34 (with vent valves 34, 24, and 15 closed), these liquids can be incubated in channel 12 by opening vent valve 15 (or optionally opening vent valve 24). By opening vent valve 15 (or 24), air would preferentially be drawn toward outlet 92 through vent valve 15 (or 24), thereby allowing the liquids to remain in place in channel 12. After sufficient incubation, vent valve 15 (or 24) could be closed, thereby causing the liquids to flow into reaction area 86. Advantageously, as illustrated in such and other embodiments, control of fluid flow can be achieved even when a substantially constant vacuum or other source of fluid flow is applied to the device.

In some embodiments, the flow of one or more fluids into an intersection or other suitable mixing region can be cut off prior to passing the entire volume of fluid to the intersection or mixing region. This may be accomplished, for example, by opening a vent valve while portions of the fluid are in the channel on opposites sides of the vent valve. For instance, a first portion of the fluid may be located in a first channel portion of an underlying channel and a second portion of the fluid may located in a second channel portion of the underlying channel, the first and second channel portions being on opposite sides of the vent valve. When the vent valve is opened while a fluid is underneath its port, a fluid from an environment external to the channel interior, such as ambient air, can be transported through the port and into the channel interior if the resistance to fluid flow of the fluid in the external environment is less than the resistance to fluid flow of the portion of the remaining portion of the fluid under the vent valve. For example, by introducing a segment of gas into the channel, the fluid contained in the channel can divide into first and second portions which are separated by the segment of gas.

Figure 3A:
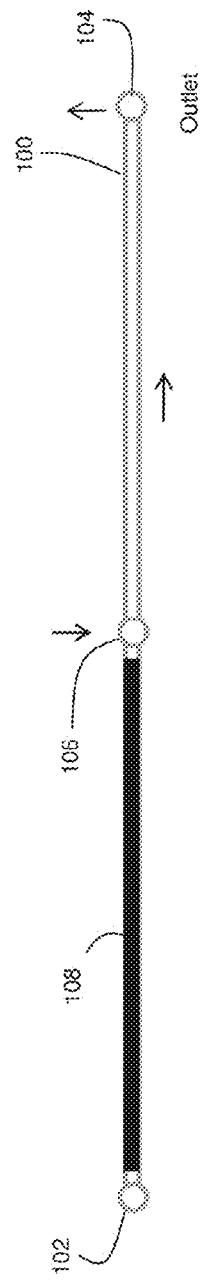
FIGS. 3A-3D include exemplary schematic diagrams of channels including one or more vent valves, according to one set of embodiments.
Figure 3B:
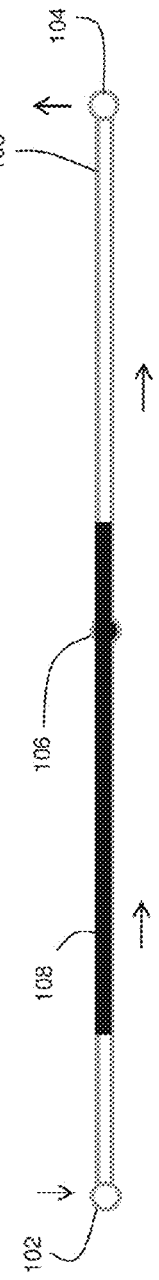
Figure 3C:
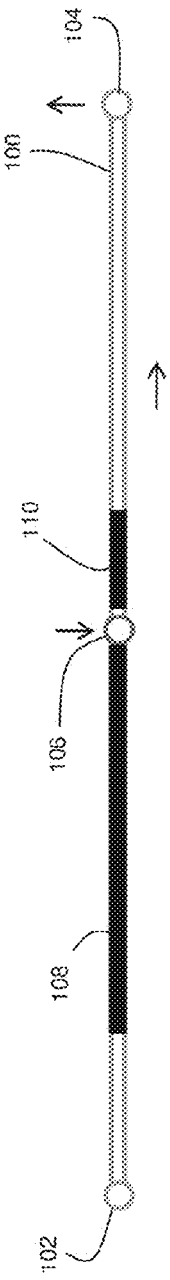
Figure 3D:
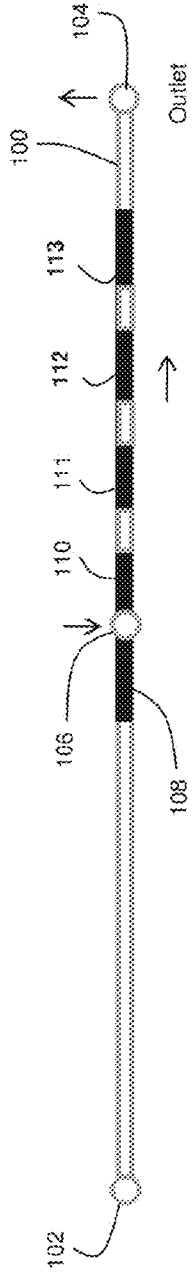

FIGS. 3A-3D include schematic illustrations of a method by which the flow of a fluid can be cut off by actuating a vent valve. In the set of embodiments illustrated in FIGS. 3A-3D, channel 100 includes inlet 102, outlet 104, and vent valve 106. In addition, channel 100 contains fluid 108. The direction of fluid flow in FIGS. 3A-3D is indicated by the arrows. In FIG. 3A, vent valve 106 is open, causing external fluid to flow into the channel via vent valve 106 when negative pressure is applied to outlet 104. In FIG. 3B, vent valve 106 is closed while inlet 102 is open, causing fluid 108 to flow through channel 100 toward outlet 104. In FIG. 3C, vent valve 106 is opened before fluid 108 has passed completely past the vent valve, causing external fluid to pass through the port of the vent valve and into the channel, separating segment 110 from fluid 108. Repeating this process can produce multiple fluid segments from an original single fluid. For example, in FIG. 3D, fluid segments 110, 111, 112, and 113 have been produced from fluid 108 by closing and opening vent valve 106 four times. Such methods can be used to produce one or more fluid portions with a pre-selected length, volume, or other suitable property.

Generating a series of fluid segments or portions from a single fluid segment can, in some cases, improve the mixing of two or more components within the fluids compared to that in the single fluid segment. For example, it is known that components (e.g., particles, reagents, or other entities) within segments of fluid, as might be observed in segmented flow, experience recirculation within the segment during linear flow of the segment. In some embodiments, a fluid containing two or more components to be mixed can be passed under a vent valve, and the vent valve can be opened and closed so as to produce multiple portions of the fluid, for example, to enhance the mixing of the two or more components within each fluid portion. This feature can be particularly advantageous in systems in which turbulent flow is absent (e.g., in many microfluidic systems).

The opening of and closing of a vent valve to create separated fluid portions can be useful outside the context of mixing as well. Multiple plugs of single reagent have been shown to be preferable to a single long plug in certain situations such as those described, for example, in International Patent Publication No. WO2005/072858 (International Patent Application Serial No. PCT/US2005/003514), filed Jan. 26, 2005 and entitled "Fluid Delivery System and Method," which is incorporated herein by reference in its entirety for all purposes. As a specific example, multiple portions of a rinsing fluid can provide better rinsing or washing of a surface compared to a single, longer fluid portion in some embodiments.

Separating a single fluid portion into two or more fluid portions can be used, in some cases, to produce a suitable volume of fluid for mixing within a mixing or other region. For example, in some cases, a first branching channel can comprise a first fluid, and a second branching channel can comprise a second fluid with a volume substantially larger than the first fluid. The first and second fluids can be flowed toward an intersection of the first and/or second branching channel and a main channel. In some embodiments, prior to passing the entire volume of the first and/or second fluid across the intersection, at least one vent valve in the first or second branching channel can be opened such that the first and/or second fluids are divided into first and second segments. In other embodiments, prior to passing the entire volume of the first and/or second fluid across the intersection, at least one vent valve in the second branching channel can be opened such that second fluid is divided into smaller segments (e.g., to match the volume of the first fluid). Only one of the segments of second fluid can be delivered to the intersection to combine with all or portions of the first fluid. These and other methods can allow, in some cases, equal or other appropriate volumes of the first and second fluids to be delivered to the main channel, a mixing region, a reaction area, or any other suitable destination (e.g., when the first and second fluids are delivered substantially simultaneously to a common region). Thus, in some embodiments, a portion, but not all, of the first fluid, and/or a portion, but not all, of the second fluid, are combined together to form a mixed fluid that is used or delivered to suitable destination.

One example of a method for delivering substantially equal volumes of multiple fluids to a common region (e.g., an intersection of two or more channels) is illustrated schematically in FIGS. 4A-4B. In FIG. 4A, main channel 200 includes outlet 202, and is fluidically connected to branching channels 204 and 206 at vent valve 208. Branching channel 204 comprises inlet 210 and contains fluid 212, while branching channel 206 comprises inlet 214 and contains fluid 216. In FIG. 4A, fluid 212 is substantially smaller in volume than fluid 216. In FIG. 4A, vent valve 208 is open, allowing exterior fluid to flow through the vent valve and through main channel 200 (as indicated by the arrows) upon application of negative pressure to the outlet. In FIG. 4B, vent valve 208 is closed, while inlets 210 and 214 are open, causing fluids 212 and 216 to flow toward outlet 202 upon application of negative pressure. In this set of embodiments, the viscosities of the fluids and the cross-sectional dimensions of channels 204 and 206 are chosen such that fluids 212 and 216 contact each other substantially simultaneously at the intersection of channels 204 and 206. In FIG. 4C, vent valve 208 is opened before fluids 212 and 216 have completely passed through the intersection of channels 204 and 206, creating a segment 218 of mixed fluid containing substantially equal parts of fluid 212 and fluid 216.

In some embodiments, multiple portions of mixed fluid can be created by opening and closing vent valve 208 any number of times. Such embodiments may be useful, for example, when fluids 212 and 216 do not initially contact each other simultaneously at the intersection of the branched channels. In some such cases, the first portion of mixed fluid can comprise more of the first than the second fluid, while subsequent portions of mixed fluid can contain substantially equal amounts of the first and second fluids. In some instances, the first portion of mixed fluid is not useful for a downstream process, so it can be diverted away from the main channel or other region of the device. For instance, an unwanted first portion of mixed fluid may be lead towards a branching channel that leads to a waste containment region. Fluid flow can be optionally controlled by the use of one or more valves (e.g., an external valve) in combination with methods described herein. One or more subsequent portions of mixed fluid, which may be useful for a downstream process, can then be delivered to the main channel or other region of the device such as reaction area.

Figure 4D:
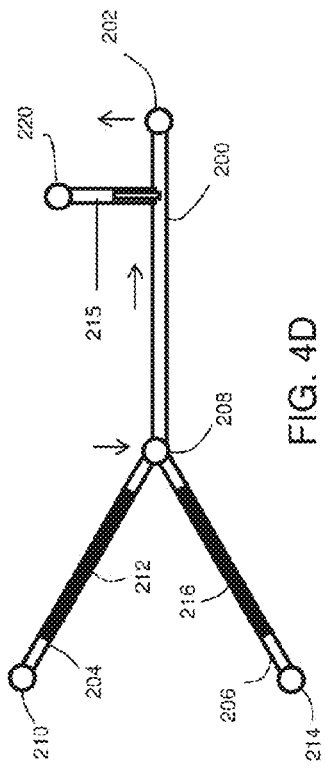
Figure 4E:
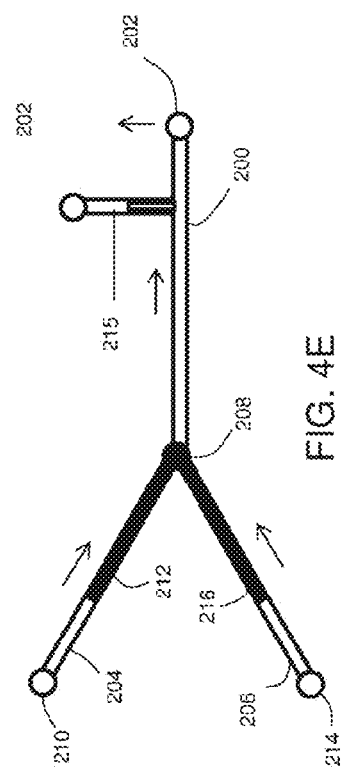
Figure 4F:
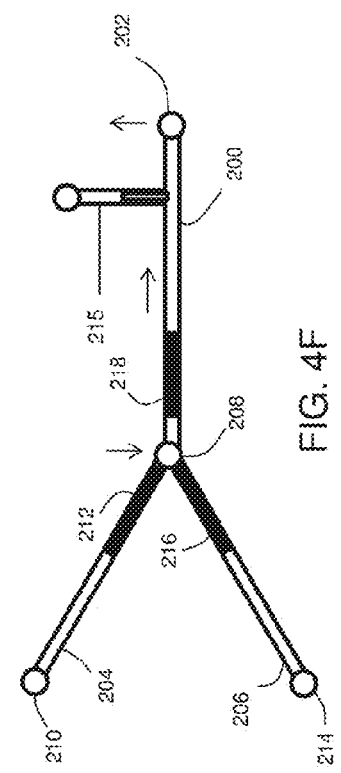

One method for diverting a portion of a mixed fluid (or any other fluid) is shown in FIGS. 4D-4I. As shown in the embodiments illustrated in FIGS. 4D-4I, a branching channel 215 having an outlet 220 is included. This outlet may be operatively associated with the same vacuum source operatively associated with outlet 202. For instance, tubing (not shown) may connect each of the outlets to the vacuum source. In some cases, a valving mechanism (not shown) is operatively associated with the tubing. Each outlet is equipped with an individually controlled valve. To combine fluids 212 and 216 to form a mixed fluid, the system is operated with outlet 202 open and outlet 220 closed (FIG. 4D). Vent valve 208 is closed (FIG. 4E) to begin mixing and then opened to deliver only a first portion of fluid 218 into main channel 220 (FIG. 4F). Once the mixed portion is in the main channel, a valving mechanism (not shown) operatively associated with the outlets is actuated to cease fluid communication between the vacuum and outlet 202, while allowing fluid communication between the vacuum and outlet 220 (FIG. 4G). Since the vacuum is now operating at outlet 220, fluid 218 can be diverted from the main channel into branching channel 215 (FIG. 4H). The valving mechanism operatively associated with the outlets can then be actuated to allow fluid communication between the vacuum and outlet 202, while ceasing fluid communication between the vacuum and outlet 220 (FIG. 4I).

Separating a single fluid portion into two or more fluid portions can provide other advantages apart from mixing fluids and producing fluid segments. For example, in some cases, when the trailing edge of a fluid reaches a vent valve, a slight burst of liquid can be ejected toward the vent valve (e.g., toward a port in the vent valve, toward an actuator associated with the vent valve, etc.). In some cases, the ejected liquid can interfere with the external valving mechanism. While, in some cases, this does not have an immediate effect on the function of the vent valve, it can, over time, lead to degradation in performance, such as, for example, contamination of the vent valve with a component (e.g., a chemical) of the fluid. Upon repeated use of the mechanism (e.g., to perform multiple experiments), such contamination can alter the normal function of the external valving mechanism. The inventors have discovered within the context of the invention that, in some embodiments, by opening the vent valve before all of the fluid has passed through the channel underneath the valve (e.g., so as to form multiple fluid segments), little or no trailing edges reach the vent valve, and no liquid ejection occurs.

The systems, devices, and methods described herein can be used, in some embodiments, to perform one or more chemical and/or biological reactions. The devices described herein can comprise additional components that may be useful for such and other purposes (e.g., blood sample analysis). In some cases, the device can comprise a reaction area which can be, for example, located downstream of a main channel. The set of embodiments illustrated in FIG. 1 includes optional reaction area 86 downstream of main channel 12. The reaction area can be fluidically connected to the outlet of the main channel (e.g., outlet 15 in FIG. 1). The reaction area can serve, for example, as a volume in which a chemical and/or biological reaction can take place. In some embodiments, a reagent and/or catalyst can be disposed within the reaction area (e.g., immobilized on a wall of the reaction area). For example, in some embodiments, a binding partner can be disposed in a reaction area (e.g., on a surface, or on or within an entity contained in the reaction area). Exemplary reaction areas that can be used in devices described herein are provided in International Patent Publication No. WO2006/113727 (International Patent Application Serial No. PCT/US06/14583), filed Apr. 19, 2006 and entitled "Fluidic Structures Including Meandering and Wide Channels" and U.S. patent application Ser. No. 12/113,503, filed May 1, 2008 and entitled "Fluidic Connectors and Microfluidic Systems" and published as U.S. Publication No. 2008/0273918; U.S. patent application Ser. No. 12/196, 392, filed Aug. 22, 2008, entitled "Liquid containment for integrated assays" and published as U.S. Publication No. 2009/0075390, which are incorporated herein by reference.

In addition, in some embodiments, a fluid waste chamber can be included, for example, downstream of the reaction area. The fluid waste chamber can be useful, for example, in providing a volume in which used fluids can be contained such that they do not flow into a negative pressure source (e.g., a vacuum) during operation of the device. For example, the set of embodiments illustrated in FIG. 1 includes waste chamber 88 that retains fluids as they are flowed from reaction area 86. Exemplary waste containment regions that can be used in devices described herein are provided in U.S. patent application Ser. No. 12/196,392, filed Aug. 22, 2008, entitled "Liquid containment for integrated assays" and published as U.S. Publication No. 2009/0075390, which is incorporated herein by reference.

In the set of embodiments illustrated in FIG. 1, a negative pressure source can be applied, for example, at any of outlet 15, point 90, and outlet 92. For example, in some cases, fluid 22 in FIG. 1 may contain a sample (e.g., a blood sample). The sample can be introduced into the device using a variety of methods. Exemplary methods and articles for sample introduction that can be used with devices described herein are provided U.S. patent application Ser. No. 12/113,503, filed May 1, 2008 and entitled "Fluidic Connectors and Microfluidic Systems" and published as U.S. Publication No. 2008/0273918; U.S. patent application Ser. No. 12/196,392, filed Aug. 22, 2008, entitled "Liquid Containment for Integrated Assays" and published as U.S. Publication No. 2009/0075390, which are incorporated herein by reference. The sample can first flow into reaction area 86, and then into waste containment region 88. The reaction area may have associated with it a detector that is capable of determining a property of a component in the reaction area. The passing of the sample through the reaction area can allow, in some cases, interaction (e.g., binding) between one or more components of the sample (e.g., an antigen) and one or more components in the reaction area (e.g., an antibody). In some embodiments, the component(s) of the reaction area may be in the form of dried reagents stored in the reaction area prior to first use. This interaction may form a product such as a binding pair complex. In some cases, this interaction alone causes a signal to be determined (e.g., measured) by a detector associated with the microfluidic system. In other cases, in order for an accurate signal to be determined by the detector, the product is treated by one or more reagents. For example, fluid may contain a labeled-antibody that interacts with an antigen of the sample. This interaction can allow the product to be labeled or the signal from the product to be amplified.

In some embodiments, the sample and/or reagent(s) are incubated within the reaction area for an amount of time. When heterogeneous affinity reactions are employed, for example, the species in the sample will bind to a capture probe immobilized on the surface of the reaction area. Sufficient incubation time can be achieved by, for example, controlling the time required for the sample to flow through the reaction area. The flow rate of the system from the vent valve to the vacuum source can be dependent upon the flow rate of the highest relative viscosity fluid through the smallest cross sectional area of channel in the system (e.g., acting as a flow bottleneck). In some embodiments, one or more properties of the system can be selected such that a desired residence time of a fluid (e.g., a sample) within the reaction area is achieved. Examples of parameters that can be adjusted to achieve residence time control include, but are not limited to, the volume of sample itself, which can be determined by the availability of sample (e.g., the volume of a drop of blood for an assay using a fingerpick of blood), or determined for convenience for the user; the viscosity of the sample; the pressure difference ($\Delta p$) applied to the outlet of the system (for application of negative pressure) or applied to the inlet of the system (for application of positive pressure); and the change in the geometry (e.g., cross-sectional area, length, etc.) and location of the flow rate bottleneck. In some embodiments, the system parameters are chosen such that the time of mixing of two or more fluids within one or more mixing regions (e.g., a vent valve) of the system is independent from the time of incubation of the sample within the reaction area.

In some cases, system parameters can be selected such that two or more fluids can be contacted with the reaction area within a predetermined period of time after mixing the two or more fluids. For example, in some embodiments, the mixed fluid can be contacted with the reaction area within 10 minutes of mixing the two or more fluids within the mixed fluid. Such embodiments can be useful, for example, when one or more components within the mixed fluid decompose and/or lose their effectiveness after a relatively short period of time. As a specific example, in some embodiments a solution of silver salts can be mixed with a reducing agent to produce an activated silver solution that can be effectively used within 10 minutes of mixing. A wide variety of reducing agents have been developed by the photographic industry and can be used in embodiments described herein. Some of the most commonly used reducing agents include: hydroquinone, chlorohydroquinone, pyrogallol, metol, 4-aminophenol and phenidone.

As can be seen, it is useful to have mixing conditions and timing independent of sample incubation times (so that longer incubation does not lead to longer mixing times). The advantages of a vent valves and methods described herein become apparent. In some cases, certain components of a fluidic system such as the dimensions of channels of the reaction area, applied pressure to induce fluid flow, etc. can be designed for whatever sample incubation time is necessary in a reaction area, and timing of mixing of reagents is controlled by one or more vent valves.

It should be appreciated that a variety of fluids can be used (e.g., disposed, flowed, stored) in association with devices described herein. In some embodiments, one or more fluids can comprise a sample to be analyzed. For example, in some cases, a fluid can comprise whole blood. In some cases, a fluid can comprise a reagent (e.g., an antibody fluid), a rinse fluid, or any other suitable fluid. In some cases, a fluid can comprise a metal solution. For example, a fluid may comprise a suspension of metal particles (e.g., silver, gold, and the like) which can form a colloidal suspension. In some cases, a fluid can comprise a reducing agent such as, for example, hydroquinone. In some embodiments, one or more of the fluids can be part of a chemical or biological assay.

Each of the fluids within a channel can have substantially similar or different chemical properties. For example, in some embodiments, a first fluid in the channel can comprise a sample to be analyzed (e.g., blood) while the second fluid comprises a rinsing solution that can be used, for example, to prepare the downstream portion for the passage of a third fluid. In some embodiments, the first fluid contains a first reagent for a chemical and/or biological reaction, and the second fluid contains a second reagent for the chemical and/or biological reaction that is different from the first reagent.

In addition, each of the fluids within the channel can have substantially similar or different physical properties. For example, in some embodiments, first and second fluids within the channel have substantially different viscosities. Differences in viscosities can cause differences in flow rate upon application of pressure to the channel.

As noted herein, in some embodiments, microfluidic systems described herein contain stored reagents prior to first use of the device and/or prior to introduction of a sample into the device. The use of stored reagents can simplify use of the microfluidic system by a user, since this minimizes the number of steps the user has to perform in order to operate the device. This simplicity can allow microfluidic systems described herein to be used by untrained users, such as those in point-of-care settings. Stored reagents in microfluidic devices are particularly useful for devices designed to perform immunoassays.

As used herein, "prior to first use of the device" means a time or times before the device is first used by an intended user after commercial sale. First use may include any step(s) requiring manipulation of the device by a user. For example, first use may involve one or more steps such as puncturing a sealed inlet to introduce a reagent into the device, connecting two or more channels to cause fluid communication between the channels, preparation of the device (e.g., loading of reagents into the device) before analysis of a sample, loading of a sample onto the device, preparation of a sample in a region of the device, performing a reaction with a sample, detection of a sample, etc. First use, in this context, does not include manufacture or other preparatory or quality control steps taken by the manufacturer of the device. Those of ordinary skill in the art are well aware of the meaning of first use in this context, and will be able easily to determine whether a device of the invention has or has not experienced first use. In one set of embodiments, devices of the invention are disposable after first use, and it is particularly evident when such devices are first used, because it is typically impractical to use the devices at all after first use.

Reagents may be stored and/or disposed in a device in fluid and/or dry form, and the method of storage/disposal may depend on the particular application. Reagents can be stored and/or disposed, for example, as a liquid, a gas, a gel, a plurality of particles, or a film. The reagents may be positioned in any suitable portion of a device, including, but not limited to, in a channel, reservoir, on a surface, and in or on a membrane, which may optionally be part of a reagent storage area. A reagent may be associated with a microfluidic system (or components of a system) in any suitable manner. For example, reagents may be crosslinked (e.g., covalently or ionically), absorbed, or adsorbed (physisorbed) onto a surface within the microfluidic system. In one particular embodiment, all or a portion of a channel (such as a fluid path of a fluid connector or a channel of the device substrate) is coated with an anti-coagulant (e.g., heparin). In some cases, a liquid is contained within a channel or reservoir of a device prior to first use and/or prior to introduction of a sample into the device.

In some embodiments, dry reagents are stored in one section of a microfluidic device and wet reagents are stored in a second section of a microfluidic device. Alternatively, two separate sections of a device may both contain dry reagents and/or wet reagents. The first and second sections may be in fluid communication with one another prior to first use, and/or prior to introduction of a sample into the device, in some instances. In other cases, the sections are not in fluid communication with one another prior to first use and/or prior to introduction of a sample into the device. During first use, a stored reagent may pass from one section to another section of the device. For instance, a reagent stored in the form of a fluid can pass from a first section to a second section of the device after the first and second sections are connected via a fluid path (e.g., a fluidic connector, as described in more detail in U.S. patent application Ser. No. 12/113,503, filed May 1, 2008 and entitled "Fluidic Connectors and Microfluidic Systems" and published as U.S. Publication No. 2008/0273918; U.S. patent application Ser. No. 12/196,392, filed Aug. 22, 2008, entitled "Liquid Containment for Integrated Assays" and published as U.S. Publication No. 2009/0075390, which are incorporated herein by reference). In other cases, a reagent stored as a dried substance is hydrated with a fluid, and then passes from the first section to the second section upon connection of the sections. In yet other cases, a reagent stored as a dried substance is hydrated with fluid, but does not pass from one section to another section upon connection of the sections.

By maintaining an immiscible fluid (a separation fluid) between each of the reagents in the reagent storage area, the stored fluids can be delivered in sequence from the reagent storage area while avoiding contact between any of the stored fluids. Any immiscible fluid that separates the stored reagents may be applied to the reaction area without altering the conditions of the reaction area. For instance, if antibody-antigen binding has occurred at one of the detection zones of the reaction area, air can be applied to the site with minimal or no effect on any binding that has occurred.

As described herein, storing reagents in a microfluidic system can allow the reagents to be dispensed in a particular order for a downstream process (e.g., amplifying a signal in a reaction area). In cases where a particular time of exposure to a reagent is desired, the amount of each fluid in the microfluidic system may be proportional to the amount of time the reagent is exposed to a downstream reaction area. For example, if the desired exposure time for a first reagent is twice the desired exposure time for a second reagent, the volume of the first reagent in a channel may be twice the volume of the second reagent in the channel. If a substantially constant pressure differential or source of fluid flow is applied in flowing the reagents from the channel to the reaction area, and if the viscosity of the fluids is the same or similar, the exposure time of each fluid at a specific point, such as a reaction area, may be proportional to the relative volume of the fluid. Factors such as channel geometry, pressure or viscosity can also be altered to change flow rates of specific fluids from the channel. The stored fluids can also be manipulated after storage (e.g., at first use) by a user using the vent valves and other articles and methods described herein.

Additionally, this strategy of storing reagents in sequence, especially amplification reagents, can be adapted to a wide range of chemistries. For example, various amplification chemistries that produce optical signals (e.g., absorbance, fluorescence, glow or flash chemiluminescence, electrochemiluminescence), electrical signals (e.g., resistance, conductivity or impedance of metal structures created by an electroless process) or magnetic signals (e.g., magnetic beads) can be used to allow detection of a signal by a detector.

Reagents can be stored in a microfluidic system for various amounts of time. For example, a reagent may be stored for longer than 1 hour, longer than 6 hours, longer than 12 hours, longer than 1 day, longer than 1 week, longer than 1 month, longer than 3 months, longer than 6 months, longer than 1 year, or longer than 2 years. Optionally, the microfluidic system may be treated in a suitable manner in order to prolong storage. For instance, microfluidic systems having stored reagents contained therein may be vacuum sealed, stored in a dark environment, and/or stored at low temperatures (e.g., refrigerated at 2-8 degree C., or below 0 degrees C.). The length of storage depends on one or more factors such as the particular reagents used, the form of the stored reagents (e.g., wet or dry), the dimensions and materials used to form the substrate and cover layer(s), the method of adhering the substrate and cover layer(s), and how the device is treated or stored as a whole.

In some embodiments, any of the inlets, outlets, and/or vent valves can be sealed prior to first use. Sealing inlets, outlets, and/or vent valves can prevent evaporation and/or contamination of fluids disposed or stored within the device. A seal over an inlet, outlet, and/or vent valve can be pierced, removed, or broken to allow external fluids to enter into the inlet and/or vent valve. As a specific example, in some embodiments, vent valve 24 and inlet 14 can be sealed prior to first use, and those seals can be pierced, removed, or broken to allow external fluids to enter. In certain embodiments, a vent valve is actuated only after the removal of a cover from a vent valve. In addition, outlet 15 (or point 90 or outlet 92) can be sealed prior to first use, and pierced, removed, or broken just prior to the application of a negative pressure (e.g., a vacuum) or to allow for venting (e.g., in the case where positive pressure is applied to the inlet).

In one particular embodiment, device 10 can be used for performing an immunoassay for human IgG, and can use sliver enhancement for signal amplification. After delivery of a sample (e.g., fluid 22) containing human IgG from channel 12 to the reaction area, binding between the human IgG and a stored dry reagent, anti-human IgG, can take place. This binding can form a binding pair complex in a detection zone (e.g., comprising a detector) proximate the reaction area. Stored reagents from upstream portions of channel 12 can then flow over this binding pair complex. One of the stored fluids (e.g., fluid 20) may include a solution of metal colloid (e.g., a gold conjugated antibody) that specifically binds to the antigen to be detected (e.g., human IgG). This metal colloid can provide a catalytic surface for the deposition of an opaque material, such as a layer of metal (e.g., a multitude of silver grains), on a surface of the detection zone. The layer of metal can be formed by using a two component system. In some cases, a metal precursor (e.g., a solution of silver salts) can be contained in fluid 62 stored in channel 36, and a reducing agent (e.g., hydroquinone, or other reducing agent listed above) can be contained in fluid 64 stored in channel 38. These two components, which can produce signal amplification upon mixing, are reactive with each others, and can only be maintained as a mixture for a few minutes. For that reason, they are stored individually and they cannot mix with each other until the flow drives both solutions towards the intersection near vent valve 34. When negative pressure is applied to outlet 92, and vent valves 24 and 34 are closed, the silver salt and hydroquinone solutions eventually merge at the intersection proximate vent valve 34, where they can mix slowly (e.g., due to diffusion) as they flow along channel 12, and then flow over the reaction area. Therefore, if antibody-antigen binding occurs in the reaction area, the flowing of the metal precursor solution through the area can result in the formation of an opaque layer, such as a silver layer, due to the presence of the catalytic metal colloid associated with the antibody-antigen complex. The opaque layer may include a substance that interferes with the transmittance of light at one or more wavelengths. Any opaque layer that is formed in the microfluidic channel can be detected optically, for example, by measuring a reduction in light transmittance through a portion of the reaction area (e.g., a meandering channel) compared to a portion of an area that does not include the antibody or antigen. Alternatively, a signal can be obtained by measuring the variation of light transmittance as a function of time, as the film is being formed in a detection zone. The opaque layer may provide an increase in assay sensitivity when compared to techniques that do not form an opaque layer.

Although immunoassays are primarily described, it should be understood that devices described herein may be used for any suitable chemical and/or biological reaction, and may include, for example, other solid-phase assays that involve affinity reaction between proteins or other biomolecules (e.g., DNA, RNA, carbohydrates), or non-naturally occurring molecules (e.g., aptamers, synthetic amino acids).

The flow of fluid within a channel can be achieved by any suitable method. In some embodiments, flow is achieved by establishing a pressure gradient within the channel in which the fluid is contained. Such a pressure gradient can be established, for example, by applying a negative pressure to one end of a channel (e.g., an outlet of a channel). Exemplary methods of applying negative pressure include, but are not limited to, attachment of a vacuum pump to an outlet, withdrawal of air from a syringe attached to an outlet, or by any other suitable method.

A pressure gradient can also be established by applying a positive pressure at one or more vent valves and a relatively smaller pressure, such as ambient pressure, at the outlet. For example, in FIGS. 4A-4C, outlet 202 may be exposed to ambient pressure. Positive pressure above ambient may be applied through an open vent valve 208, which would result in fluid flow in the direction of the arrows shown in FIG. 4A, as long as inlets 210 and 214 remained closed. As shown illustratively in FIG. 4B, vent valve 208 can be closed and inlets 210 and 214 opened to pressure above ambient. To move a mixed plug of fluid as shown in FIG. 4C, inlets 210 and 214 can be closed while 208 is reopened to positive pressure. The use of positive pressure may involve closing all of the vent valves associated with the device, except those on the desired path of flow. The closure of any vent valve may be fluid tight. Positive pressure can be applied, for example, via a pump, by use of gravity, or any other suitable method.

In certain embodiments, the pressure applied to induce fluid flow (e.g., a positive or negative pressure) from a fluid flow source (e.g., a vacuum or a pump) remains substantially constant during the carrying out of a process (e.g., a reaction) in the device after initial application of the fluid flow source to the channel system, even when valves and/or other components described herein are actuated. However, the linear flow rate of fluids in the channel can vary, and may be controlled by various methods such as those described in U.S. patent application Ser. No. 12/428,372, filed Apr. 22, 2009, entitled "Flow Control in Microfluidic Systems" and published as U.S. Publication No. 2009/0266421, which is incorporated herein by reference. In other embodiments, the pressure from a source of fluid flow can be varied during operation of the device.

In some embodiments, a chemical and/or biological reaction involves binding. Different types of binding may take place in devices described herein. The term "binding" refers to the interaction between a corresponding pair of molecules that exhibit mutual affinity or binding capacity, typically specific or non-specific binding or interaction, including biochemical, physiological, and/or pharmaceutical interactions. Biological binding defines a type of interaction that occurs between pairs of molecules including proteins, nucleic acids, glycoproteins, carbohydrates, hormones and the like. Specific examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc.

In some cases, a heterogeneous reaction (or assay) may take place in a channel; for example, a binding partner may be associated with a surface of a channel, and the complementary binding partner may be present in the fluid phase. The term "binding partner" refers to a molecule that can undergo binding with a particular molecule. Biological binding partners are examples; for instance, Protein A is a binding partner of the biological molecule IgG, and vice versa. Likewise, an antibody is a binding partner to its antigen, and vice versa. In other cases, a homogeneous reaction may occur in the channel. For instance, both binding partners can be present in the fluid phase (e.g., in two-fluid laminar flow system). Non-limiting examples of typical reactions that can be performed in a meandering channel system include chemical reactions, enzymatic reactions, immuno-based reactions (e.g., antigen-antibody), and cell-based reactions.

A device can be fabricated of any material suitable. Non-limiting examples of materials include polymers (e.g., polyethylene, polystyrene, polycarbonate, poly(dimethylsiloxane), PMMA, PFFE, a cyclo-olefin copolymer (COC), and cyclo-olefin polymer (COP)), glass, quartz, and silicon. Those of ordinary skill in the art can readily select a suitable material based upon e.g., its rigidity, its inertness to (e.g., freedom from degradation by) a fluid to be passed through it, its robustness at a temperature at which a particular device is to be used, and/or its transparency/opacity to light (e.g., in the ultraviolet and visible regions). In some embodiments, the material and dimensions (e.g., thickness) of a substrate are chosen such that the substrate is substantially impermeable to water vapor.

In some instances, a microfluidic substrate is comprised of a combination of two or more materials, such as the ones listed above. For instance, the channels of the device may be formed in a first material (e.g., poly(dimethylsiloxane)), and a cover that is formed in a second material (e.g., polystyrene) may be used to seal the channels. In another embodiment, a channels of the device may be formed in polystyrene or other polymers (e.g., by injection molding) and a biocompatible tape may be used to seal the channels. A variety of methods can be used to seal a microfluidic channel or portions of a channel, including but not limited to, the use of adhesives, gluing, bonding, welding (e.g., ultrasonic) or by mechanical methods (e.g., clamping).

A channel can have any cross-sectional shape (circular, semi-circular, oval, semi-oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and outlet(s). A channel may also have an aspect ratio (length to average cross sectional dimension) of at least 2:1, more typically at least 3:1, 5:1, or 10:1 or more. An open or partially open channel, if present, may include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (e.g., a concave or convex meniscus).

Though in some embodiments, systems of the invention may be microfluidic, in certain embodiments, the invention is not limited to microfluidic systems and may relate to other types of fluidic systems. "Microfluidic," as used herein, refers to a device, apparatus or system including at least one fluid channel having a cross-sectional dimension of less than 1 mm, and a ratio of length to largest cross-sectional dimension of at least 3:1. A "microfluidic channel," as used herein, is a channel meeting these criteria.

The "cross-sectional dimension" (e.g., a diameter) of the channel is measured perpendicular to the direction of fluid flow. Most fluid channels in components of the invention have maximum cross-sectional dimensions less than 2 mm, and in some cases, less than 1 mm. In one set of embodiments, all fluid channels containing embodiments of the invention are microfluidic or have a largest cross sectional dimension of no more than 2 mm or 1 mm. In another set of embodiments, the maximum cross-sectional dimension of the channel(s) containing embodiments of the invention are less than 500 microns, less than 200 microns, less than 100 microns, less than 50 microns, or less than 25 microns. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used.

In some instances, a reagent is positioned in a channel prior to complete fabrication of a microfluidic channel system. A microfluidic channel system is not complete if, for example, a system that is designed to have enclosed channels has channels that are not yet completely enclosed. A channel is enclosed if at least one portion of the channel has a cross-section that is completely enclosed, or if the entire channel is completely enclosed along its entire length with the exception of its inlet(s) and/or outlet(s).

Wet reagents are typically stored in a microfluidic system after channels of the system have been completely covered. A fluid reagent to be stored in the system may be introduced into an inlet of a channel, and after at least partially filling the channel with the fluid, the inlet(s) and/or outlet(s) of the channel can be sealed, for example, to retain the fluid and to prevent contamination from external sources.

The term "determining," as used herein, generally refers to the measurement and/or analysis of a substance (e.g., within a reaction site), for example, quantitatively or qualitatively, or the detection of the presence or absence of the substance. "Determining" may also refer to the measurement and/or analysis of an interaction between two or more substances, for example, quantitatively or qualitatively, or by detecting the presence or absence of the interaction.

A variety of determination (e.g., measuring, quantifying, detecting, and qualifying) techniques may be used. Determination techniques may include optically-based techniques such as light transmission, light absorbance, light scattering, light reflection and visual techniques. Determination techniques may also include luminescence techniques such as photoluminescence (e.g., fluorescence), chemiluminescence, bioluminescence, and/or electrochemiluminescence. Those of ordinary skill in the art know how to modify microfluidic devices in accordance with the determination technique used. For instance, for devices including chemiluminescent species used for determination, an opaque and/or dark background may be preferred. For determination using metal colloids, a transparent background may be preferred. Furthermore, any suitable detector may be used with devices described herein. For example, simplified optical detectors, as well as conventional spectrophotometers and optical readers (e.g., 96-well plate readers) can be used.

EXAMPLES

The following examples are intended to illustrate certain embodiments of the present invention, but do not exemplify the full scope of the invention.

Example 1

Methods for fabricating a microfluidic channel system are described.

Channel systems, such as the ones shown in FIGS. 1A and 1B, were designed with a computer-aided design (CAD)

program. The microfluidic devices were formed in poly (dimethylsiloxane) Sylgard 184 (PDMS, Dow Corning, Ellsworth, Germantown, Wis.) by rapid prototyping using masters made in SU8 photoresist (MicroChem, Newton, Mass.). The masters were produced on a silicon wafer and were used to replicate the negative pattern in PDMS. The masters contained two levels of SU8, one level with a thickness (height) of ~70 µm defining the channels in the immunoassay area, and a second thickness (height) of ~360 µm defining the reagent storage and waste containment regions. Another master was designed with channel having a thickness (height) of 33 µm. The masters were silanized with (tridecafluoro-1,1,2,2-tetrahydrooctyl)trichlorosilane (ABC-R, Germany). PDMS was mixed according to the manufacturer's instructions and poured onto the masters. After polymerization (4 hours, 65° C.), the PDMS replica was peeled off the masters and access ports were punched out of the PDMS using stainless steel tubing with sharpened edges (1.5 mm in diameter). To complete the fluidic network, a flat substrate such as a glass slide, silicon wafer, polystyrene surface, flat slab of PDMS, or an adhesive tape was used as a cover and placed against the PDMS surface. The cover was held in place either by van der Waals forces, or fixed to the microfluidic device using an adhesive.

In other embodiments, the microfluidic channels were made in polystyrene, cyclo-olefin-copolymer, or other thermoplastics by injection molding. This method is known to those of ordinary skill in the art. The volume of an injection molding cavity can be defined by a bottom surface and a top surface separated by a hollow frame which determines the thickness of the molded article. For an article including channel features and or other microscale elements on two opposing sides of the article, the bottom and top surfaces of the molding cavity may include raised features that create the channel features on either side of the article. For an article including channel features on only one side of the article, only the top or bottom surface of the molding cavity includes such features. Thru-holes that pass through the entire thickness of the article can be produced by pins traversing the cavity, embedded in one or more surfaces of the cavity and contacting the other side. For instance, the pins may extend from only the top surface, only the bottom surface, or from both the top and bottom surfaces. When the cavity is filled with pressurized, molten plastic and then cooled, an article is created with channels on one or both sides and holes serving as connectors or inlets and outlets. To complete the fluid network, adhesive tape was applied to the surfaces of the article to seal the channels.

Example 2

This example describes the control of movement of fluids in microfluidic systems comprising a single channel that incorporate at least one vent valve to control the movement of fluid. FIGS. 5A-5B include schematic illustrations of the systems described in this example.

The system shown in FIG. 5A includes a single channel in which an inlet, an outlet, a vent valve were fabricated. This system was fabricated by injection molding as described in Example 1. The single channel 302 was configured to flow fluid portions 304 and 306 in the direction of arrow 308. Water was used for the fluid portions 304 and 306 in this experiment, and these fluid portions were separated by a plug of air. The channel included vent valve 310 and inlet 312 upstream of vent valve 310. A vacuum operating at a substantially constant pressure of −40 kPa was applied at channel outlet 314 to provide a pressure drop across the microfluidic channel during the entire experiment.

When vent valve 310 was opened, it functioned as a preferential vent, meaning air flowed through the valve to replace the fluid leaving the system through the outlet. Fluids located upstream of vent valve 310 (including the fluid between valve 310 and inlet 312) did not flow regardless of whether the inlet was open or closed. When vent valve 310 was closed, all of the fluid in the channel flowed as long as inlet 312 was open. In this way, vent valve 310 was used to control delivery of a fluid in a microfluidic channel. Note that when both vent valve 310 and inlet 312 were closed, no fluid flowed through the channel (although some motion was observed due to fluid expansion when vacuum was applied).

The system shown in FIG. 5B includes a single channel in which three vent valves were incorporated. The single channel 320 was configured to flow fluid portions 322, 324, 326, and 328 in the direction of arrow 308. The channel included inlet 330 and vent valves 332, 334, and 336. Like the system described in FIG. 5A, a vacuum was applied at channel outlet 340 to provide a pressure drop across the microfluidic channel.

In one experiment, vent valve 332 was opened and, upon applying the vacuum to outlet 340, only fluid 322 was transported through channel 320. Subsequently, vent valve 332 was closed while valve 334 was opened, resulting in the transport of only fluid 324 through channel 320. Next, vent valves 332 and 334 were closed while valve 336 was opened, and fluid portion 326 was transported through the channel. Finally, vent valves 332, 334, and 336 were closed while inlet 330 was opened, resulting in the transport of fluid portion 328 through the channel.

In another set of experiments, multiple fluids were transported through the channel simultaneously. In one case, prior to first use, vent valve 332 was closed, but valve 334 was opened. Upon applying vacuum to the outlet 340, fluid portions 322 and 324 were simultaneously transported through channel 320 in the direction of arrow 308. In another experiment, prior to first use, vent valves 332 and 334 were closed, but valve 336 was opened. Upon applying vacuum to the outlet 340, fluid portions 322, 324, and 326 were simultaneously transported through channel 320 in the direction of arrow 308. Finally, in one experiment, all of the vent valves were closed, and inlet 330 was opened, resulting in the simultaneous transport of fluid portions 322, 324, 326, and 328, upon applying vacuum to the outlet 340.

This example shows that fluid control, including the timing of fluid plugs, can be achieved in a device by opening and closing one or more vent valves and by applying a single source of fluid flow (e.g., a vacuum) operated at a substantially constant pressure throughout the use of the device.

Example 3

This example describes the control of movement of fluids in microfluidic systems comprising multiple channels and at least one vent valve to control the movement of fluid. FIGS. 6A-6C include schematic illustrations of the systems described in this example. In the device illustrated in FIG. 6A, a microchannel 410 was fluidically connected to two channel branches 412 and 414, which intersected at vent valve 416. Microchannel 410 contained fluid 418. In addition, fluids 420 and 422 were stored in branches 412 and 414, respectively. Channel 410 was connected to outlet 424, while branches 412 and 414 were connected to inlets 426 and 428, respectively. All of the fluids in the device were separated by plugs of gas (immiscible with fluid 418, 420 and 422).

A vacuum operating at a substantially constant pressure of −40 kPa during the entire experiment was attached to outlet 424. Initially, vent valve 416 was opened, which caused fluid 418 to flow through microchannel 410 in the direction of arrow 408 and air to flow through vent valve 416. Fluids 420 and 422 did not move even though inlets 426 and 428 were open. After fluid 418 exited outlet 424, the flow rate of the gas through vent valve 416 increased, due to the elimination of the pressure drop caused by fluid 418. Next, vent valve 416 was closed. Once the vent valve was closed, fluids 420 and 422 were mixed at vent valve 416 to produce mixed fluid 430 (shown in FIG. 6B).

In another set of experiments, fluids 420 and 422 were transported sequentially, rather than simultaneously, past vent valve 416. In a first experiment, in the embodiment illustrated in FIG. 6C, vent valve 416 and inlet 426 were both closed (while inlet 428 was opened) after fluid 418 was transported through outlet 424. By closing inlet 426, fluid 420 was held substantially stationary in branch 412 due to the inability of gas to enter inlet 426. On the other hand, fluid 422 was transported through branch 414 and past closed vent valve 416 as gas was transported through inlet 428.

This example shows that fluid control, including mixing and the timing of fluid plugs, can be achieved in a device by opening and closing one or more vent valves and by applying a single source of fluid flow (e.g., a vacuum) operated at a substantially constant pressure throughout the use of the device.

Example 4

Figure 7:
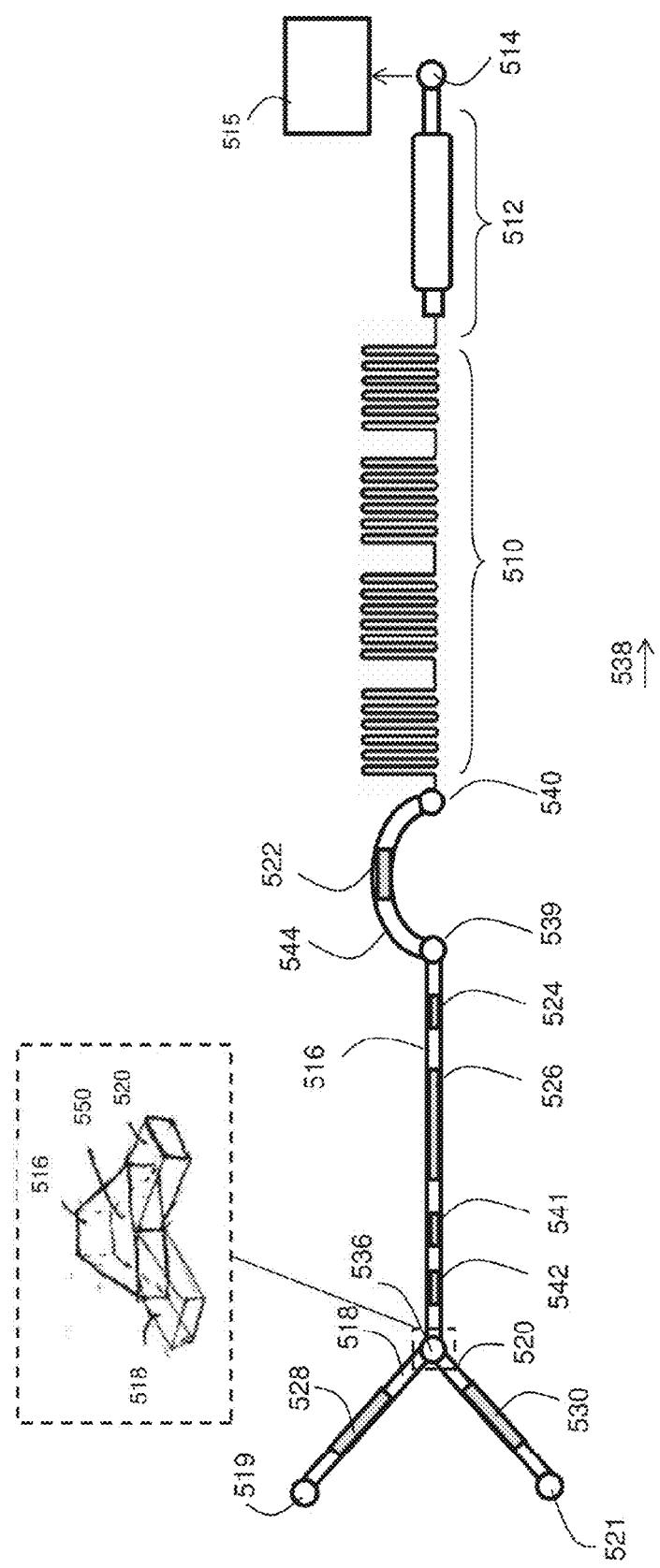
FIG. 7 includes an exemplary schematic illustration of a device including a plurality of detection regions, according to one set of embodiments.

This example describes the use of a branched channel system to perform an assay in which an optically detectable signal by electrolessly depositing silver onto gold particles. FIG. 7 includes a schematic illustration of the assay device 300 used in this example. The assay used in this example is generally described in International Patent Publication No. WO2005/066613 (International Patent Application Serial No. PCT/US2004/043585), filed Dec. 20, 2004 and entitled "Assay Device and Method," which is incorporated herein by reference in its entirety for all purposes.

The device included reaction area 510, waste containment region 512, and an outlet 514. The reaction area included a microfluidic channel 50 microns deep and 120 microns wide, with a total length of 175 mm. The device also included microfluidic channel 516 and channel branches 518 and 520 (with inlets 519 and 521, respectively). Channel 516 and branches 518 and 520 were 350 microns deep and 500 microns wide. In addition, channel 516 was 390 mm long, and branches 518 and 520 were each 360 mm long. The reaction area and microfluidic channels were fabricated as described in Example 1. Before sealing the channels, anti-PSA antibodies were attached to a surface of the device in a segment of the reaction area 510.

Prior to first use, the device was loaded with liquid reagents. The following sequence of liquids were loaded into channel 516: a 2 microliter plug of water 542, a 2 microliter plug of buffer solution 541, a 20 microliter plug of aqueous solution containing anti-PSA antibodies labeled with colloidal gold 526, a microliter plug of buffer solution 524. This sequence of fluid plugs was loaded using a pipette through the inlet port 539. Fluid 528, containing a solution of silver salt, was loaded into branching channel through port 519 using a pipette. Fluid 530, containing a reducing solution, was loaded into branching channel 520 through port 521. Each of the liquids shown in FIG. 7 were separated from the other liquids by plugs of air. Ports 514, 519, 521, 536, 539, and 540 were sealed with an adhesive tape that can be easily removed or pierced. As such, the liquids were stored in the device prior to first use.

At first use, the ports 514, 519, 521, 536, 539, and 540 were unsealed. A tube 544 containing 10 microliters of sample blood (522) was connected to ports 539 and 540. This created a fluidic connection between reaction area 510 and channel 516, which were otherwise unconnected and not in fluid communication with one another prior to first use. A vacuum of −40 kPa was applied to port 514 using a negative pressure source 515. Sample 522 was flowed in the direction of arrow 538 into reaction area 510. As the fluid passed through the reaction area, the PSA proteins in sample 522 were captured by anti-PSA antibodies immobilized on the reaction area walls. The sample took 5 minutes to pass through the reaction area, after which it was captured in the waste containment region 512. Exemplary waste containment regions that can be used in devices described herein are provided in U.S. patent application Ser. No. 12/196,392, filed Aug. 22, 2008, entitled "Liquid containment for integrated assays" and published as U.S. Publication No. 2009/0075390, which is incorporated herein by reference.

Fluids 524, 526, 541, and 542 followed the sample through the reaction area 510 towards waste containment region 512. This resulted in the transport of fluid 524 in the direction of arrow 538 to reaction area 510. As fluid 524 was passed through the reaction area, it washed away remaining unbound sample components. As fluid 526 passed through the reaction area, gold-labeled anti-PSA antibodies were coupled to the PSA captured on the reaction area walls (to form a sandwich immunocomplex). Fluids 541 and 542 followed and further washed the reaction area of any unbound reagent component. The last wash fluid 542 (water) washed away salts that could react with silver salts (i.e., chloride, phosphate, azide).

Silver can be deposited on the captured gold particles to increase the size of the colloids to amplify the signal. In some embodiments, the signal can be recorded by optical means as optical density. To accomplish this, fluids 528 and 530 were mixed to produce a reactive silver solution. The ratio of the volumes of fluids 528 and 530 was about 1:1. To initiate the mixing of fluids 528 and 530, vent valve 536 was closed while the vacuum applied at 514 was maintained, resulting in the simultaneous flow of fluids 528 and 530 towards vent valve 536. The vent valve was closed to initiate mixing only after the final previous fluid 542 had exited the reaction area. Closure was performed in one experiment by sealing port 536 with an adhesive tape. In another experiment, a tube (not shown) operatively associated with a solenoid valve (SMC V124A-6G-M5, not shown) was connected to vent valve 536 with an o-ring tight fit. The solenoid valve was activated to seal the port (and later deactivated to unseal the port) in a manner similar to that described herein with respect to FIGS. 2E-2F. Fluids 528 and 530 mixed with each other at vent valve 536, producing an activated silver solution with a viscosity of about $1 \times 10^{-3}$ Pa s. The cross-sectional area of the microfluidic channel under vent valve 536 (i.e., a mixing region 550) was about twice that of channels 518 and 520 as illustrated in the inset. After 10 seconds, vent valve 536 was opened. At that time, approximately 55% of both fluids 528 and 530 had mixed, and the remaining fluids 528 and 530 were left in channels 518 and 520, respectively.

The activated silver solution was flowed through reaction area 510 to provide the silver for the deposition. Because the mixed solution is stable for only a few minutes (usually less than 10 minutes) the mixing was performed less than a minute before use in reaction area 510. Moreover, in order to achieve a reproducible deposition of silver on the colloids, the time between mixing of the reagents to produce the activated silver solution and the delivery of the activated silver solution to the reaction area were controlled such that they were consistent among multiple experiments.

The control of the flow rates of the fluids within channel 516 and the reaction area 510 were important when flowing fluids through the system. Due to the reaction area's relatively small cross sectional area, it served as a bottleneck, controlling the overall flow rate in the system. When the reaction area contained liquids, the linear flow rates of the fluids in channel 516 was about 0.5 mm s$^{-1}$. Fluids flowing from branching channels 518 and 520 into main channel 516 might not have mixed reproducibly at this rate, as one fluid might have flowed faster than the other, causing unequal portions of fluids 528 and 530 to be mixed. On the other hand, when the reaction area contained air, the linear flow rates of the fluids in channel 516 and branching channels 518 and 520 were about 15 mm s$^{-1}$. At this higher flow rate, the flow rate in branching channels 518 and 520 were equal and reproducible (when vent valve 536 was closed), producing reproducible mixing. For this reason, vent valve 536 was not closed until fluid 542 passed through the reaction area to the waste containment region. One could determine when fluid 542 had exited the reaction area 510 visually (by eye). Alternatively, an optical detector was positioned so as to measure transmission of light through part of reaction area 510, as described in more detail in more detail in International Patent Publication No. WO2005/066613 (International Patent Application Serial No. PCT/US2004/043585), filed Dec. 20, 2004 and entitled "Assay Device and Method", which is incorporated herein by reference.

The microfluidic system shown in FIG. 7 was designed such that the volume of the channel between vent valve 536 and reaction area 510 was larger than the expected volume of the mixed activated silver solution (i.e., the combined portion of fluids 528 and 530 which traveled into channel 516 while vent valve 536 was closed). This ensured that substantially all of the mixing took place at a relatively high linear flow rate (since no liquid, and only air, was present in the reaction area 510 at this time), and before the activated solution reached the reaction area. This configuration helped promote reproducible and equal mixing.

For the assay described in this example, it was important to sustain a flow of the activated silver mixture within the reaction area for a few minutes (e.g., 2 to 10 minutes). In a first experiment, 45 microliter volumes of fluids 528 and 530 were loaded, of which a portion was used for mixing (producing a total of 55 microliters of activated silver solution). This volume of combined fluid had a residence time in the reaction area of about 300 seconds. However, the use of this relatively small volumes of liquid could pose a challenge. When relatively short lengths of fluid segments 528 and 530 are used, it can be relatively difficult to ensure that 1:1 ratios of the two fluids were mixed. Small variations in segment length could produce uneven flow rates of the two liquids, with a shorter segment exhibiting a relatively high flow rate (due to a relatively small resistance to flow and) compared to the longer segment. This effect can produce a deviation in mixing ratio.

Figure 8:
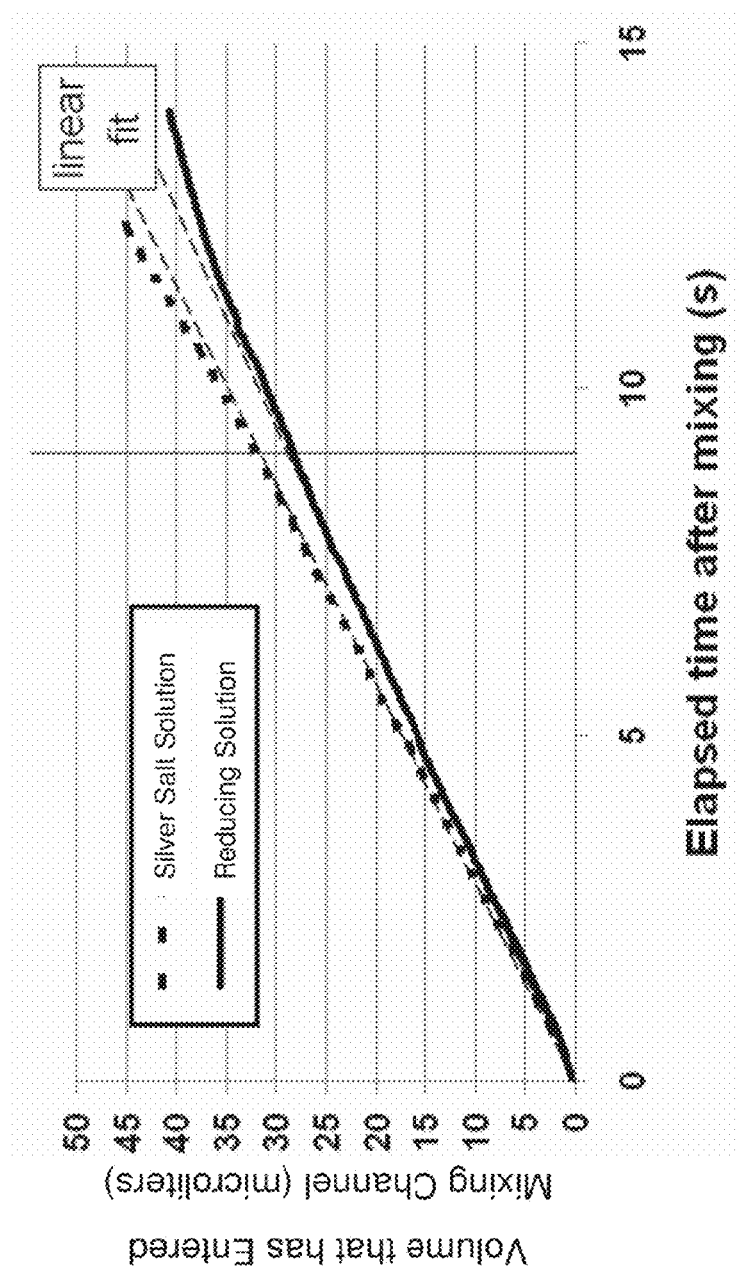
FIG. 8 includes a plot of cumulative volume of mixed fluid as a function of time, according to one set of embodiments.

To characterize this effect, a second set of experiments was performed in which a 45 microliter volume of silver salt solution and a 45 microliter volume of reducing solution were mixed to produce a 90 microliter volume of activated silver solution. The silver salt solution was found to flow slightly faster (for a combination of reasons including slight differences in formulation, due to the difference in chemical composition, and slight variation in channel cross section, due to the tolerances of the machining techniques used for the channel fabrication) relative to the reducing solution, and therefore, exhibited a slightly faster flow rate through its branch when the vacuum was applied. FIG. 8 includes a plot of the volumes of the silver salt solution (dotted line) and the reducing solution (solid line) that have entered the mixing channel (in microliters) as a function of the time elapsed after the initial contact of the silver salt and reducing solutions. This difference in flow rate is indicated by the slight difference in the slope of the lines in FIG. 8 from t=0 to t=9 seconds. At t=9 seconds, the absolute difference in lengths of the segments becomes important, and the silver salt solution (having a faster flow rate, and thus a shorter segment of liquid remaining in its branch) flowed even faster relative to the reducing solution. This effect is illustrated by upward trend of the silver salt curve (relative to the linear extrapolation), and the downward trend of the reducing solution curve.

In addition, it was observed that if the trailing edge of one of fluids 528 and 530 reagents reached vent valve 536, a slight burst of liquid was ejected toward the top of the hole in vent valve 536. That liquid was found to enter into contact with the external valving mechanism. While this had no immediate observable effect on the valving efficiency, it resulted in unwanted contamination of the valve. Repeated use of the valve in this manner (e.g., to run multiple experiments) might alter the normal function of the valve. By re-opening vent-valve 536 before all of fluids 528 and 530 have mixed ensured that neither of the trailing edges of fluids 528 and 530 reached vent valve 526, and no liquid ejection occurred. Thus, by loading excess reagent into branches 518 and 520 (to ensure there are no large variations between the lengths of fluids 528 and 530 during flow), and by using no more than about ⅔ of the volume of the stored reagent before re-opening vent valve 536, a consistent mixing ratio was maintained throughout the mixing step while avoiding liquid projection/contamination of the external valving mechanism in vent valve 536. The valve may be re-opened at various stages of completion depending of the flow behavior of a specific set of reagents.

This example shows that fluid control, including the mixing of reagents, the changing of flow rates, and the timing of fluid flow can be achieved in a device to perform an assay by opening and closing one or more vent valves and by applying a single source of fluid flow (e.g., a vacuum) operated at a substantially constant pressure throughout the use of the device. This example also shows the importance of controlling flow rates of individual plugs of fluid to be mixed in a device.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A device comprising:
   an upstream microfluidic channel portion having a cross-sectional dimension of less than 1 mm;
   a first liquid positioned in the upstream microfluidic channel portion;
   a downstream microfluidic channel portion having a cross-sectional dimension of less than 1 mm;
   a second liquid positioned in the downstream microfluidic channel portion;
   a component of a vent valve comprising a port positioned between the upstream and downstream microfluidic channel portions; and
   a removable seal sealing the port,
   wherein the device can be configured such that when the port is in an open position, the second liquid in the downstream microfluidic channel portion can be flowed without substantially flowing the first liquid, and when the port is in a closed position, the first liquid from the upstream microfluidic channel portion can be flowed to the downstream microfluidic channel portion.

2. A device as in claim 1, wherein the device is sealed and constructed and arranged for storing the first liquid in the device.

3. A device as in claim 2, wherein the upstream microfluidic channel portion contains a third liquid stored therein, and wherein the first and third liquids are separated by a fluid substantially immiscible with both the first and third liquids.

4. A device as in claim 2, wherein the device is sealed and constructed and arranged for storing the first liquid and the second liquid in the device while the first and second liquids are in fluid communication with one another.

5. A device as in claim 1, comprising a first microfluidic branching channel and a second microfluidic branching channel, and wherein the upstream microfluidic channel portion is part of one of the first or second microfluidic branching channels.

6. A device as in claim 5, wherein the first and second branching channels connect at an intersection and are fluidically connected to the downstream channel portion.

7. A device as in claim 5, wherein the first liquid is positioned in the first microfluidic branching channel, and the device comprises a third liquid positioned in the second microfluidic branching channel.

8. A device as in claim 6, wherein the intersection of the first and second microfluidic branching channels comprises a mixing region, the mixing region having a larger cross-sectional area than either of the first or second microfluidic branching channels.

9. A device as in claim 1, wherein the first liquid comprises a metal solution, and wherein the upstream microfluidic channel portion contains a third liquid, the third liquid comprising a reducing agent.

10. A device as in claim 1, wherein the device comprises a second component of a second vent valve comprising a second port positioned along the upstream microfluidic channel portion or the downstream microfluidic channel portion.

11. A device as in claim 1, wherein the second liquid is different from the first liquid.

12. A device as in claim 1, wherein the second liquid is the same as the first liquid.

13. A device as in claim 1, wherein the downstream microfluidic channel portion comprises multiple rinse solutions separated by one or more gases.

14. A device as in claim 1, wherein the first liquid and/or second liquid comprises a rinse solution.

15. A device as in claim 1, wherein the first and second liquids are separated by a third liquid substantially immiscible with both the first and second liquids.

16. A device as in claim 1, wherein at least one of the first and second liquids contains a reagent for a chemical and/or biological reaction.

17. A device as in claim 16, wherein the reagent participates in a heterogeneous affinity reaction.

18. A device as in claim 1, comprising a valving mechanism adapted and arranged to open and close the port.

19. A device comprising:
   an upstream microfluidic channel portion having a cross-sectional dimension of less than 1 mm;
   a first liquid positioned in the upstream microfluidic channel portion;
   a downstream microfluidic channel portion having a cross-sectional dimension of less than 1 mm;
   a second liquid positioned in the downstream microfluidic channel portion;
   a port positioned between the upstream and downstream microfluidic channel portions, wherein the port can be configured to be opened and closed in a vent valve arrangement; and
   a removable seal sealing the port,
   wherein the device can be configured such that when the port is in an open position, the second liquid in the downstream microfluidic channel portion can be flowed without substantially flowing the first liquid, and when the port is in a closed position, the first liquid from the upstream microfluidic channel portion can be flowed to the downstream microfluidic channel portion.

20. A method, comprising:
   in a device comprising an upstream microfluidic channel portion having a cross-sectional dimension of less than 1 mm and containing a first liquid, a downstream microfluidic channel portion having a cross-sectional dimension of less than 1 mm and containing a second liquid, a component of a vent valve comprising a port positioned between the upstream and downstream microfluidic channel portions, and a removable seal sealing the port, performing the steps of:
   unsealing the port;
   flowing the second liquid in the downstream microfluidic channel portion without substantially flowing the first liquid; and
   flowing the first liquid from the upstream microfluidic channel portion to the downstream microfluidic channel portion after the flowing of the second liquid.

* * * * *